(12) United States Patent
Osborne et al.

(10) Patent No.: US 10,813,972 B2
(45) Date of Patent: Oct. 27, 2020

(54) TREATMENT OF DNA DAMAGE AND MITOCHONDRIAL DYSFUNCTION USING PALM FRUIT JUICE

(71) Applicants: BRANDEIS UNIVERSITY, Waltham, MA (US); MALAYSIAN PALM OIL BOARD, Kajang (MY)

(72) Inventors: Adam E. Osborne, Waltham, MA (US); Lawrence J. Wangh, Auburndale, MA (US); Kenneth C. Hayes, Wellesley Hills, MA (US); Ravigadevi Sambanthamurthi, Petaling Jaya (MY)

(73) Assignees: MALAYSIAN PALM OIL BOARD, Selangor, Kajang (MY); BRANDEIS UNIVERSITY, Waltham, MA (US)

( * ) Notice: Subject to any disclaimer, the term of this patent is extended or adjusted under 35 U.S.C. 154(b) by 1046 days.

(21) Appl. No.: 14/766,215

(22) PCT Filed: Feb. 6, 2014

(86) PCT No.: PCT/US2014/015110
§ 371 (c)(1),
(2) Date: Aug. 6, 2015

(87) PCT Pub. No.: WO2014/124140
PCT Pub. Date: Aug. 14, 2014

(65) Prior Publication Data
US 2016/0000854 A1 Jan. 7, 2016

Related U.S. Application Data

(60) Provisional application No. 61/761,473, filed on Feb. 6, 2013, provisional application No. 61/791,162, filed on Mar. 15, 2013.

(51) Int. Cl.
| | | |
|---|---|---|
| A61K 36/889 | (2006.01) | |
| A61K 31/192 | (2006.01) | |
| A61K 31/7072 | (2006.01) | |
| G01N 33/68 | (2006.01) | |
| A23L 33/105 | (2016.01) | |
| A61K 31/4409 | (2006.01) | |
| C12Q 1/6883 | (2018.01) | |

(52) U.S. Cl.
CPC .......... A61K 36/889 (2013.01); A23L 33/105 (2016.08); A61K 31/192 (2013.01); A61K 31/4409 (2013.01); A61K 31/7072 (2013.01); C12Q 1/6883 (2013.01); G01N 33/6842 (2013.01); *A23V 2002/00* (2013.01); *C12Q 2600/156* (2013.01)

(58) Field of Classification Search
CPC ..................................................... A61K 36/889
USPC .......................................................... 424/727
See application file for complete search history.

(56) References Cited

U.S. PATENT DOCUMENTS

| | | | |
|---|---|---|---|
| 6,156,738 A | 12/2000 | Bell et al. | |
| 6,881,854 B2 | 4/2005 | Ptock et al. | |
| 7,387,802 B2 | 6/2008 | Sambanthamurthi et al. | |
| 8,470,861 B2* | 6/2013 | Anders ................... | A61K 31/19 514/385 |
| 2003/0031740 A1 | 2/2003 | Sambanthamurthi et al. | |
| 2008/0193603 A1 | 8/2008 | Hayes et al. | |
| 2009/0252817 A1* | 10/2009 | Hayes .................. | A61K 31/192 424/725 |
| 2010/0278943 A1 | 11/2010 | Sambanthamurthi et al. | |
| 2012/0040014 A1 | 2/2012 | Settineri et al. | |

FOREIGN PATENT DOCUMENTS

| | | | |
|---|---|---|---|
| CN | 101815516 A | 8/2010 | |
| CN | 105377283 A | 3/2016 | |
| JP | 2011518131 A | 6/2011 | |
| WO | 2002101086 A2 | 12/2002 | |
| WO | 2009014417 A2 | 1/2009 | |
| WO | WO-2009014417 A2 * | 1/2009 | ........... A61K 36/889 |
| WO | 2009146102 A1 | 12/2009 | |
| WO | 2014124140 A1 | 8/2014 | |

OTHER PUBLICATIONS

Asuncion, et al. ("AZT Treatment Induces Molecular and Ultrastructural Oxidative Damage to Muscle Mitochondria", Journal Clinical Investigation, vol. 102, No. 1, Jul. 1998, 4-9). (Year: 1998).*
De la Asuncion, et. al., "AZT Treatment Induces Molecular and Ultrastructural Oxidative Damage to Muscle Mitochondia", J. Clin. Invest., vol. 102, No. 1, Jul. 1998, 4-9, Especially abstract.
Sundram, et al., "FTN 29: Composition and nutritional characteristics of water soluble antioxidant rich extract from oil palm processing", Proceedings of the International Palm Oil Congress (PIPOC), Food Technology and Nutrition Conference, Hotel Istana, Kuala Lumpur, Malaysia, Aug. 20-22, 2001, pp. 250-253.
Tan, et. al., "Valorisation of palm by-products as functional components", Eur. J. Lipid Sci. Technol. 109 (2007) 380-393.
Wattanapenpaiboon BSc, et. al., "Phytonutrient defiency: the place of palm fruit", Asia Pacific J. Clin. Nutr. 2003; 12 (3): 363-368.

(Continued)

*Primary Examiner* — Michael Barker
*Assistant Examiner* — Deborah A Davis
(74) *Attorney, Agent, or Firm* — Troutman Pepper Hamilton Sanders LLP (Rochester)

(57) ABSTRACT

Methods, compositions and kits for the prevention and treatment of mitochondrial dysfunction, mitochondrial DNA damage and genomic DNA damage are provided. The methods use the administration of palm fruit juice and/or compositions containing phenolic compounds present in palm fruit juice. The methods, compositions, and kits can be used to reduce DNA damage in subjects being treated with nucleoside reverse transcriptase inhibitors, such as patients having HIV or AIDS.

9 Claims, 4 Drawing Sheets
Specification includes a Sequence Listing.

(56) References Cited

OTHER PUBLICATIONS

Balasundram MSc, et. al., "Antioxidant properties of palm fruit extracts", Asia Pacific J. Clin. Nutr. 2005; 4 (4): 319-324.
Rolo, et. al., "Diabetes and mitochondrial function: Role of hyperglycemia and oxidative stress", Toxicology and Applied Pharamacology, Apr. 15, 2006, vol. 212, No. 2, pp. 167-178, Especially p. 170, col. 1, para 1; p. 172 col. 1 para 3; p. 173, col. 2 para 3.
Igarashi, et. al., "Effects of Dietary Catechins on Glucose Tolerance, Blood Pressure and Oxidative Status in Goto-Kakizaki Rats", J Nutr Sci Vitaminol, 53, 496-500, 2007.
Chin BSc., et. al., "Reduction of DNA damage in older healthy adults by Tri E Tocotrienol supplementation", Elsevier, Nutrition 24 (2008) 1-10.
Sun, et. al., "γ-Tocotrienol induces mitochondria-mediated apoptosis in human gastric adenocarcinoma SGC-7901 cells", Journal of Nutritional Biochemistry 20 (2009) 276-284.
Rajavel, et. al., "Chronic administration of oil palm (*Elaeis guineenis*) leaves extract attenuates hyperglycaemic-induced oxidative stress and improves renal histopathology and function in experimental diabetes", Evidence-Based Complementary and Alternative Medicine, Aug. 6, 2012, vol. 2012, 12 pages, Abstract, p. 2, col. 1, para 3: p. 2, col. 2, para 1; p. 5, col. 1, para 4; p. 9, col. 2, para 1.
Wu Shu-Jing et. al., "Antioxidant and Antiepatoma Activities of Palm Oil Extract", Journal of Food Lipids, 2007, vol. 14, pp. 122-137. See abstract; p. 123, line 16-p. 123, line 23, p. 123, line 32-p. 123, line 34.
Balasundram N., et. al., "Antioxidants from palm (*Elaeis guineensis*) fruit extracts", Asia Pacific J. Clin. Nutr. 2003; vol. 12, Suppl.: S37. See the whole document.
Wei, Z., "A Study of Antituberculosis Drug-induced Mitochondrial Injury in Liver Cells of Mice", a Master degree thesis of North China Coal University Medical University, Medical Science and Technology Special of CMFD (electronic journal), 2012, No. 2, Mar. 15; the abstract, pp. 29-31, point 4, p. 32, point 6; Relevant to Claim No. 77-82.
Abeywardena, M., et al., "Polyphenol-enriched extract of oil palm fronds (*Elaeis guineensis*) promotes vascular relaxation via endothelium-dependent mechanisms", Asia Pacific Journal Clin. Nutr., 2002, vol. 11, Suppl 7:S467-S472.
Archibald, "Antioxidant Products: Nutritional Science and Marketplace Opportunities," Prepared Foods 2007, May supplement. Retrieved from the Internet: <URL: http://www.panelamonitor.org/documents/159/antioxidant-products-nutritional-science-and-marke/.
Attele et al., "Antidiabetic Effects of Panax ginseng Berry Extract and the Identification of an Effective Component," Diabetes, vol. 51, Jun. 2002, pp. 1851-1858.
Aucott et al., "Weight loss in obese diabetic and non-diabetic individuals and long-term diabetes outcomes—a systematic review," Diabetes, Obesity and Metabolism, vol. 6, 2004, pp. 85-94.
Aviram et al., "Pomegranate juice consumption reduces oxidative stress, atherogenic modifications to LDL, and platelet aggregation: studies in humans and in atherosclerotic apolipoprotein E-deficient mice," Am J Clin Nutr, vol. 71, 2000, pp. 1062-1076.
Harrison, Lau Lik Nang, et al., "Extraction and Identification of Water-Soluble Compounds in Palm-Pressed Fiber," American Journal of Environmental Sciences, vol. 3(2): pp. 54-59 (2007).
El-Alfy et al., "Protective effect of red grape seeds proanthocyanidins against induction of diabetes by alloxan in rats," Pharmacological Research, vol. 52, 2005, pp. 264-270.
Hayes, et al., "The complex interplay of palm oil fatty acids on blood lipids," Eur. J. Lipid Sci. Technol. 2007, 109(4), pp. 453-464.
Hosoda et al., "Antihyperglycemic Effect of Oolong Tea in Type 2 Diabetes," Diabetes Care, vol. 26, No. 6, Jun. 2003, pp. 1714-1718.
Lakka et al., "The Metabolic Syndrome and Total and Cardiovascular Disease Mortality in Middle-aged Men," JAMA, vol. 288, No. 21, Dec. 4, 2002, pp. 2709-2716.
Ludvik et al., "Efficacy of Ipomoea batatas (Caiapo) on Diabetes Control in Type 2 Diabetic Subjects Treated With Diet," Diabetes Care, vol. 27, No. 2, Feb. 2004, pp. 436-440.
Refinetti, "The Nile Grass Rat as a Laboratory Animal," Lab Animal, vol. 33, No. 9, Oct. 2004, pp. 54-57. ***Abstract Only***.
Singh et al., "Attenuation of hyperglycemia and associated biochemical parameters in STZ-induced diabetic rats by dietary supplementation of potato peel powder," Clinica Chimica Acta, vol. 353, 2005, pp. 165-175. ***Abstract Only***.
Wu et al., "Green tea supplementation ameliorates insulin resistance and increases glucose transporter IV content in a fructose-fed rat model," European Journal of Nutrition, vol. 43, No. 2, 2004, pp. 116-124. ***Abstract Only***.
Xie et al., "American Ginseng Berry Juice Intake Reduces Blood Glucose and Body Weight in ob/ob Mice," Journal of Food Science, vol. 72, No. 8, 2007, pp. S590-S594.
Zunino et al., "Diets Rich in Polyphenols and Vitamin A Inhibit the Development of Type I Autoimmune Diabetes in Nonobese Diabetic Mice," The Journal of Nutrition, vol. 137, 2007, pp. 1216-1221.
Edem, D.O., "Palm oil: Biochemical, physiological, nutritional, hematological, and toxicological aspects: A review," Plant Foods for Human Nutrition, 57:319-341 (2002).
Elaeis guineenis Jacq. (Source James A Duke, 1983. Handbook of Energy Crops and website article www.hort.purdue.edu/newcrop/duke_energy/elaesis_guineensidhtml).
European Patent Application No. 14749028.8, Extended European Search Report (dated Oct. 13, 2016).
Chen et al., "[Studies on the Antitumor Effect of Trachycarpus fortunei Fruit Extraction], " Strait Pharmaceut. J. 24 (6):265-67 (2012).
PCT/US2014/015110, International Preliminary Report on Patentability (dated Aug. 11, 2015).
PCT/US2014/015110, International Search Report and Written Opinion (dated Apr. 17, 2014).

\* cited by examiner

TREATMENT OF DNA DAMAGE AND MITOCHONDRIAL DYSFUNCTION USING PALM FRUIT JUICE

CROSS-REFERENCE TO RELATED APPLICATIONS

This application claims priority to U.S. Provisional Application No. 61/761,473, entitled "Palm Fruit Juice Supplement and Methods for Using Same", filed 6 Feb. 2013, and to U.S. Provisional Application No. 61/791,162, entitled "Treatment of DNA Damage and Mitochondrial Dysfunction Using Palm Fruit Juice", filed 15 Mar. 2013. Each of these provisional applications is incorporated by reference herein in its entirety.

BACKGROUND

Mitochondria produce most of the ATP needed for cellular function. There are hundreds of mitochondria per cell, with each mitochondrion containing several copies of its own genome (mtDNA). The human mitochondrial genome is a 16,569 base circular piece of DNA that encodes for 13 genes of the electron transport chain, 22 tRNAs, and two rRNAs. This genome also contains a control region (the D-Loop), that contains two hyper-variable regions (HV1 and HV2). All the other necessary factors and electron transport chain proteins are encoded in the nucleus and transported into the mitochondria.

Mitochondrial dysfunction and mtDNA damage increase over time and are associated with numerous diseases, including Parkinson's, diabetes and familial deafness. Characteristics of mitochondrial dysfunction include an increase in reactive oxygen species (ROS), a decrease in ATP production, a decrease in synthesis of electron transport chain proteins, and changes to mitochondrial size, shape, and membrane potential. Mitochondrial dysfunction may be caused by the gradual accumulation of mitochondrial mutations.

In addition to being associated with aging and disease, mitochondrial dysfunction and mtDNA damage are also side effects of certain drugs used to treat various diseases, including HIV/AIDS, tuberculosis, general infections, and cancer. For example, treatment of HIV/AIDS with antiretroviral drugs, such as Nucleoside Reverse Transcriptase Inhibitors (NRTIs), can cause mitochondrial damage. Certain NRTIs are designed to inhibit viral reverse transcriptase, but also inhibit mitochondrial polymerase γ, the sole DNA polymerase in the mitochondria, thereby blocking the replication of mtDNA. This results in depletion of mtDNA in the mitochondria, leading to mitochondrial dysfunction. Other NRTIs that do not cause depletion of mitochondrial DNA, such as 3'-Azido-3'-deoxythymidine (AZT, also known as ZDV), may still cause mitochondrial dysfunction through another pathway. Specifically, AZT may damage mtDNA through the build-up of a monophosphorylated form of AZT, which inhibits proofreading during DNA replication and/or by causing an increase in ROS, which in turn increases the rate of mtDNA mutation.

In light of the foregoing, there is a need for novel compositions and methods for the prevention and treatment of mitochondrial dysfunction and DNA damage, particularly in susceptible populations, such as the elderly and individuals being treated with NRTIs and other drugs.

SUMMARY OF THE INVENTION

Provided herein are methods, compositions and kits for the prevention and treatment of mitochondrial dysfunction, mitochondrial DNA damage and/or genomic DNA damage.

One aspect of the invention is a method of treating or preventing mitochondrial dysfunction and/or mitochondrial DNA (mtDNA) damage in a subject. In certain embodiments the method includes administering to a subject in need thereof a composition containing an extract (e.g., a water soluble extract or dried reagents) from a fruit of the genus *Elaeis* or a composition containing the phenolics (e.g., one or more natural phenolics or synthetic versions of those phenolics) present in such an extract. In some embodiments the composition contains natural phenolics, such as cinnamate and/or benzoate. In some embodiments the composition includes an extract from the vegetation liquor resulting from the palm oil milling process.

In some embodiments of the method the subject has been administered an agent that increases the risk of and/or causes a mitochondrial disorder and/or mtDNA damage. In certain embodiments the subject has been administered a Nucleoside Reverse Transcriptase Inhibitor (NRTI), such as 3'-azido-3'-deoxythymidine (AZT). In some embodiments the subject is infected with HIV and/or has AIDS.

In certain embodiments the subject has a mitochondrial disease or disorder.

In some embodiments the subject has an age-related disease or disorder.

In some embodiments, the subject has or is suspected of having a mtDNA mutation. In some embodiments the method also includes the step of determining whether the subject has a mtDNA mutation. In some embodiments the determining step includes the performance of an amplification reaction (e.g., PCR) and/or a sequencing assay (e.g., chain termination sequencing, sequencing by ligation, sequencing by synthesis, pyrosequencing, ion semiconductor sequencing, single-molecule real-time sequencing, and/or 454 sequencing). In some embodiments the determining step is performed using LATE-PCR/Lights-On/Lights-Off/PCR-Perfect technology.

Another aspect of the invention is a method of treating or preventing genomic DNA damage in a subject. In certain embodiments the method includes administering to a subject in need thereof a composition containing an extract (e.g., a water soluble extract) from a fruit of genus *Elaeis* or a composition containing the phenolics (e.g., natural or synthetic phenolics) present in such an extract. In some embodiments the composition contains natural phenolics, such as cinnamate and/or benzoate. In some embodiments the composition includes an extract from the vegetation liquor of the palm oil milling process.

In some embodiments of the method the subject has or is predisposed to developing cancer. In certain embodiments the subject has been exposed to a condition that increases the likelihood of genomic DNA damage.

In certain embodiments the subject has or is suspected of having a genomic DNA mutation. In some embodiments the method also includes the step of determining whether the subject has a genomic DNA mutation. In some embodiments the determining step includes the performance an amplification reaction (e.g., PCR). In some embodiments the determining step includes the performance of a sequencing assay (e.g., chain termination sequencing, sequencing by ligation, sequencing by synthesis, pyrosequencing, ion semiconductor sequencing, single-molecule real-time sequencing, and/or 454 sequencing). In some embodiments the determining step is performed using LATE-PCR/Lights-On/Lights-Off/PCR-Perfect technology.

Yet another aspect of the invention is a method of treating a subject for HIV and/or AIDS. In certain embodiments the method includes administering to a subject in need thereof a composition containing an extract (e.g., a water soluble extract) from a fruit of genus *Elaeis* or a composition containing the phenolics (e.g., natural or synthetic phenolics) present in such an extract. In some embodiments the method also includes administering to the subject an NRTI, such as AZT. In some embodiments the composition contains natural phenolics, such as cinnamate and/or benzoate. In some embodiments the composition includes an extract from the vegetation liquor of the palm oil milling process. In some embodiments provided herein is a kit for treating or preventing mitochondrial dysfunction, mtDNA damage and/or genomic DNA damage in a subject comprising an extract (e.g., a water soluble extract) from a fruit of genus *Elaeis* or a composition comprising the phenolics (e.g., synthetic phenolics) present in such an extract. In some embodiments the extract contains phenolics, such as cinnamate and/or benzoate. In some embodiments the extract is from the vegetation liquor of the palm oil milling process.

DETAILED DESCRIPTION OF THE INVENTION

General

Figure 1A:
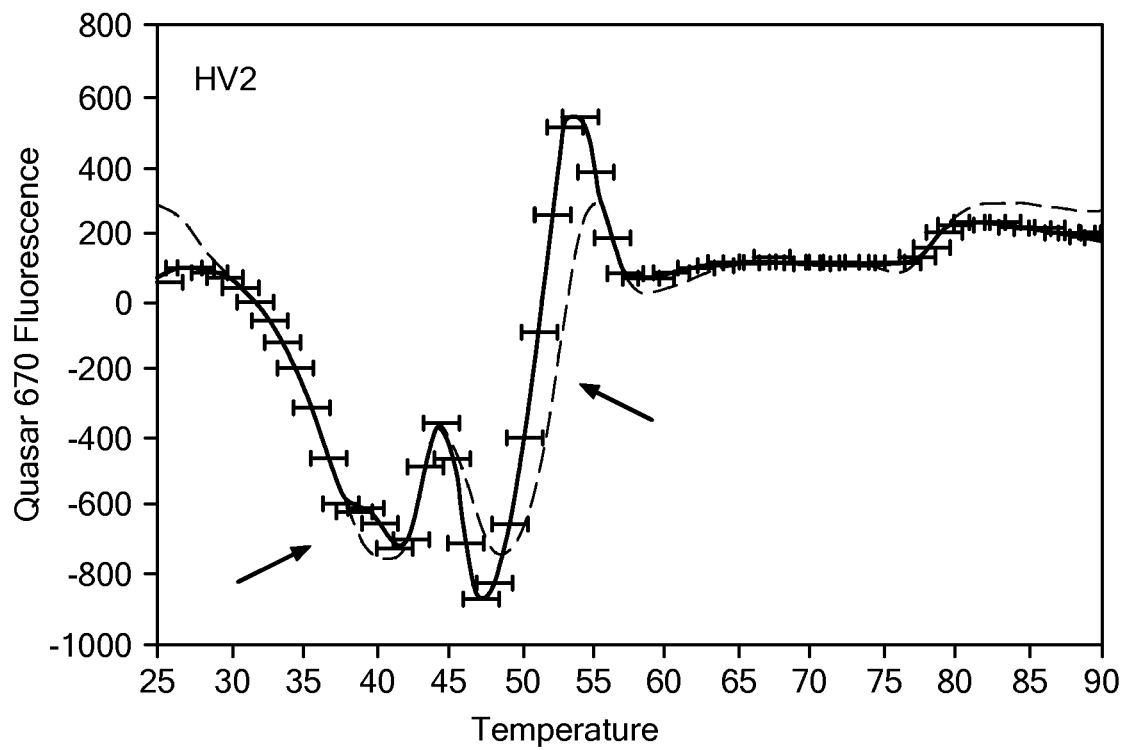
FIGS. 1A, 1B, and 1C show the fluorescent signature shifts indicative of AZT-induced mutations in the mitochondrial DNA for each of the three targets HV2, CO2, and ND1, respectively. The black line indicates the reference sequence and the gray line represents the shifted signature. Arrows indicate areas of difference and evidence of the mutation. Error bars represent three standard deviations from the mean reference.

Provided herein are methods and kits for treating and/or preventing mitochondrial dysfunction, mitochondrial DNA (mtDNA) mutations and/or genomic DNA mutations. In some embodiments, the methods provided herein include the administration and/or consumption of palm fruit juice (PFJ) in its entirety and/or administered as the bioactive compounds contained therein (e.g., the phenolics, extracted from natural sources or synthetically manufactured).

Palm fruit juice contains phenolics that act as antioxidants. These antioxidants act to reduce the amount of reactive oxygen species (ROS) in cells, and in the mitochondria within cells. The genomic DNA and mitochondrial DNA within cells can become mutated due to excess accumulation of ROS, which can lead to mitochondrial dysfunction and various diseases, such as cancer, diabetes and Alzheimer's disease. Drugs used to treat bacterial infections and viral infections, including, but not limited to, streptomycin, isoniazid, cyclosporin A, neomycin and nucleoside reverse transcriptase Inhibitors (NRTIs), can cause mitochondrial damage. One of the most commonly used NRTIs is AZT, which can also cause damage to the mitochondrial genome.

Furthermore, components in PFJ can interact with cellular entities (DNA polymerases, RNA polymerases, transcription factors, epigenetic machinery) to mitigate/prevent DNA damage and/or mitochondrial dysfunction.

Palm fruit juice and the phenolics contained within PFJ reduce DNA damage, including the mitochondrial damage caused by AZT and other genotoxic drugs. PFJ and the polyphenols in PFJ are therefore useful, for example, in preventing ROS mediated mitochondrial DNA damage caused by various agents and natural phenomena including aging and disease.

In some embodiments, provided herein is a method of treating or preventing mitochondrial dysfunction and/or mitochondrial DNA (mtDNA) damage in a subject. In certain embodiments the method includes administering to the subject a composition containing an extract (e.g., a water soluble extract) from a fruit of genus *Elaeis* or a composition containing the phenolics (e.g., natural or synthetic phenolics) present in such an extract. In some embodiments the composition contains natural phenolics, such as cinnamate and/or benzoate. In some embodiments the composition includes an extract from the vegetation liquor of the palm oil milling process. In some embodiments the composition is in a nutraceutical or pharmaceutical composition. In certain embodiments the nutraceutical or pharmaceutical composition further comprises an essential fatty acid, an antioxidant, a vitamin, or a mineral. In some embodiments the nutraceutical or pharmaceutical composition further comprises γ-linolenic acid, linoleic acid, zinc, copper, selenium, iodide, pyridoxine, folate, cobalamin, coenzyme $Q_{10}$, vitamin C, vitamin $B_1$, vitamin E, thiamin diphosphate, vitamin $B_6$, vitamin $B_{12}$, vitamin D, manganese, vitamin A, riboflavin, niacin, niacinamide, pantothenic acid, biotin, inositol, choline bitartrate, betaine, vitamin K, molybdenum, chromium, potassium, citrus bioflavonoids, mixed carotenoids, green tea extract, or N-acetylcysteine.

In some embodiments the subject has been administered an agent that increases the risk of and/or causes mitochondrial disorders and/or mtDNA damage. In certain embodiments the subject has been administered an NRTI such as 3'-azido-3'-deoxythymidine (AZT). In some embodiments the subject is infected with HIV and/or has AIDS. In other embodiments the subject has been administered an antitubercular agent (e.g. IHN) or combination of agents In certain embodiments the subject has a mitochondrial disease or disorder. In some embodiments the mitochondrial disease or disorder is mitochondrial myopathy, diabetes mellitus and deafness (DAD), Leber's hereditary optic neuropathy (LHON), Leigh syndrome, neuropathy, ataxia, retinitis pigmentosa and petosis (NARP), myoclonic epilepsy with ragged red fibers (MERRF), myoneurogenic gastrointestinal encephalopathy (MNGIE), mitochondrial myopathy, encephalomyopathy, lactic acidosis, stroke-like symptoms (MELAS), Kearns-Sayre syndrome (KSS), chronic progressive external opthalmoplegia (CPEO) and/or mtDNA depletion.

In some embodiments the subject has an age-related disease or disorder. In certain embodiments the age-related disease or disorder is Alzheimer's disease, amyotrophic lateral sclerosis, arthritis, atherosclerosis, cachexia, cancer, cardiac hypertrophy, cardiac failure, cardiac hypertrophy, cardiovascular disease, cataracts, colitis, chronic obstructive pulmonary disease, dementia, diabetes mellitus, frailty, heart disease, hepatic steatosis, high blood cholesterol, high blood pressure, Huntington's disease, hyperglycemia, hypertension, infertility, inflammatory bowel disease, insulin resistance disorder, lethargy, metabolic syndrome, muscular dystrophy, multiple sclerosis, neuropathy, nephropathy, obesity, osteoporosis, Parkinson's disease, psoriasis, retinal degeneration, sarcopenia, sleep disorders, sepsis and/or stroke.

In some embodiments, the subject has or is suspected of having a mtDNA mutation. In some embodiments the method also includes the step of determining whether the subject has a mtDNA mutation. In some embodiments the determining step includes the performance of an amplification reaction (e.g., PCR or LATE-PCR) and/or a sequencing assay (e.g., chain termination sequencing, sequencing by ligation, sequencing by synthesis, pyrosequencing, ion semiconductor sequencing, single-molecule real-time sequencing, and/or 454 sequencing). In some embodiments the determining step is performed using LATE-PCR/Lights-On/Lights-Off/PCR-Perfect technology.

In some embodiments, disclosed herein is a method of treating or preventing genomic DNA damage in a subject. In certain embodiments the method includes administering to the subject a composition containing a water-soluble extract from plant, such as the fruit of genus *Elaeis* or a composition containing the phenolics (e.g., natural or synthetic phenolics) present in a water-soluble extract from a fruit of genus *Elaeis*. In some embodiments the composition contains natural phenolics, such as cinnamate and/or benzoate. In some embodiments the composition includes an extract from the vegetation liquor of the palm oil milling process. In some embodiments the composition is in a nutraceutical or pharmaceutical composition. In certain embodiments the nutraceutical or pharmaceutical composition further comprises an essential fatty acid, an antioxidant, a vitamin, or a mineral. In some embodiments the nutraceutical or pharmaceutical composition further comprises γ-linolenic acid, linoleic acid, zinc, copper, selenium, iodide, pyridoxine, folate, coenzyme $Q_{10}$, cobalamin, vitamin C, vitamin $B_1$, vitamin E, thiamin diphosphate, vitamin $B_6$, vitamin $B_{12}$, vitamin D, manganese, vitamin A, riboflavin, niacin, niacinamide, pantothenic acid, biotin, inositol, choline bitartrate, betaine, vitamin K, molybdenum, chromium, potassium, citrus bioflavonoids, mixed carotenoids, green tea extract, or N-acetylcysteine.

In some embodiments the subject has or is predisposed to cancer. In certain embodiments the subject has been exposed to a condition that increases the likelihood of genomic DNA damage. In certain embodiments the subject has been exposed to elevated levels of ionizing radiation. In some embodiments the subject has undergone radiation therapy. In some embodiments the subject has been exposed to and/or consumed a mutagen. In some embodiments the mutagen is selected from the group consisting of acetaldehyde, aflatoxins, 4-aminobiphenyl, areca nut, aristolochic acid, arsenic, asbestos, azathioprine, benzene, benzidine, benzo[a]pyrene, beryllium, betel quid, bis(chloromethyl)ether, busulfan, 1,3-butadiene, cadmium, chlorambucil, chlornaphazine, chromium (VI) compounds, clonorchis sinensis, cyclophosphamide, cyclosporine, diethylstilbestrol, erionite, ethylene oxide, etoposide, formaldehyde, ionizing radiation, melphalan, methoxsalen, 4,4'-methylenebis(chloroaniline), MOPP, 2-naphthylamine, neutron radiation, nickel compounds, N'-nitrosonornicotine, 4-(N-nitrosomethylamino)-1-(3-pyridyl)-1-butanone, 3,4,5,3',4'-pentachlorobiphenyl, 2,3,4,7,8-pentachlorodibenzofuran, phenacetin, phosphorus-32, plutonium, radioiodines, radionuclides, radium-224, radium-226, radium-228, radon-222, semustine, shale oils, sulfur mustard, 2,3,7,8-tetrachlorodibenzo-para-dioxin, thiotepa, thorium-232, ortho-toluidine, treosulfan and vinyl chloride.

In certain embodiments the subject has or is suspected of having a genomic DNA mutation. In some embodiments the method also includes the step of determining whether the subject has a genomic DNA mutation. In some embodiments the determining step includes the performance an amplification reaction (e.g., PCR or LATE-PCR). In some embodiments the determining step includes the performance of a sequencing assay (e.g., chain termination sequencing, sequencing by ligation, sequencing by synthesis, pyrosequencing, ion semiconductor sequencing, single-molecule real-time sequencing, and/or 454 sequencing). In some embodiments the determining step is performed using LATE-PCR/Lights-On/Lights-Off/PCR-Perfect technology.

In some embodiments, disclosed herein is a method of treating a subject for HIV and/or AIDS. In certain embodiments the method includes administering to the subject a composition containing a water-soluble extract from a fruit of genus *Elaeis* or a composition containing the phenolics (e.g., natural or synthetic phenolics) present in a water-soluble extract from a fruit of genus *Elaeis*. In some embodiments the method also includes administering to the subject an NRTI, such as AZT. In some embodiments the composition contains natural phenolics, such as cinnamate and/or benzoate. In some embodiments the composition includes an extract from the vegetation liquor of the palm oil milling process. In some embodiments the composition is in a nutraceutical or pharmaceutical composition. In certain embodiments the nutraceutical or pharmaceutical composition further comprises an essential fatty acid, an antioxidant, a vitamin, or a mineral. In some embodiments the nutraceutical or pharmaceutical composition further comprises γ-linolenic acid, linoleic acid, zinc, copper, selenium, iodide, pyridoxine, folate, cobalamin, coenzyme $Q_{10}$, vitamin C, vitamin $B_1$, vitamin E, thiamin diphosphate, vitamin $B_6$, vitamin $B_{12}$, vitamin D, manganese, vitamin A, riboflavin, niacin, niacinamide, pantothenic acid, biotin, inositol, choline bitartrate, betaine, vitamin K, molybdenum, chromium, potassium, citrus bioflavonoids, mixed carotenoids, green tea extract, or N-acetylcysteine. In some embodiments provided herein is a kit for treating or preventing mitochondrial dysfunction, mtDNA damage and/or genomic DNA damage in a subject comprising a water-soluble extract from a fruit of genus *Elaeis* or a composition comprising the phenolics (e.g., synthetic phenolics) present in a water-soluble extract from a fruit of genus *Elaeis*. In some embodiments the extract contains phenolics, such as cinnamate and/or benzoate. In some embodiments the extract is from the vegetation liquor of the palm oil milling process. In some embodiments the kit also includes an NRTI, such as AZT. In some embodiments the extract is in a nutraceutical or pharmaceutical composition. In certain embodiments the nutraceutical or pharmaceutical composition further comprises an essential fatty acid, an antioxidant, a vitamin, or a mineral. In some embodiments the nutraceutical or pharmaceutical composition further comprises γ-linolenic acid, linoleic acid, zinc, copper, selenium, iodide, pyridoxine, folate, cobalamin, coenzyme $Q_{10}$, vitamin C, vitamin $B_1$, vitamin E, thiamin diphosphate, vitamin $B_6$, vitamin $B_{12}$, vitamin D, manganese, vitamin A, riboflavin, niacin, niacinamide, pantothenic acid, biotin, inositol, choline bitartrate, betaine, vitamin K, molybdenum, chromium, potassium, citrus bioflavonoids, mixed carotenoids, green tea extract, or N-acetylcysteine.

Definitions

As used herein, the term "administering" means providing a nutraceutical or pharmaceutical agent or composition to a subject, and includes, but is not limited to, administering by a medical professional and self-administering.

The term "agent" is used herein to denote a chemical compound, a small molecule, a mixture of chemical compounds and/or a biological macromolecule (such as a nucleic acid, an antibody, an antibody fragment, a protein or a peptide). Agents may be identified as having a particular activity by screening assays described herein below. The activity of such agents may render them suitable as a "therapeutic agent" which is a biologically, physiologically, or pharmacologically active substance (or substances) that acts locally or systemically in a subject.

As used herein, the term "cancer" includes, but is not limited to, solid tumors and blood-born tumors. The term cancer includes diseases of the skin, tissues, organs, bone, cartilage, blood and vessels. The term "cancer" further encompasses primary and metastatic cancers.

As used herein, the term "nutraceutical" generally means any food that provides an additional benefit other than its nutritional benefit.

As used herein, the term "subject" means a human or non-human animal selected for treatment or therapy. A subject "in need of" administration of a composition according to the invention is a subject who has or is suspected of having any of the diseases, disorders, or conditions described herein for which a method of the invention is provided to treat, prevent, aid in treating, or aid in preventing the disease, disorder, or condition.

The phrases "therapeutically-effective amount" and "effective amount" as used herein mean the amount of an agent which is effective for producing the desired therapeutic effect in at least a sub-population of cells in a subject at a reasonable benefit/risk ratio applicable to any medical treatment.

"Treating" a disease or condition in a subject or "treating" a subject having a disease or condition refers to subjecting the subject to a nutraceutical or pharmaceutical treatment, e.g., the administration of a pharmaceutical or nutraceutical composition, such that at least one symptom of the disease or condition is decreased or prevented from worsening.

"Preventing" a disease or condition in a subject refers to performing an action with regard to the subject, e.g., administering a pharmaceutical or nutraceutical composition to the subject, that reduces the probability that the subject will develop the disease or condition compared to the absence of such action.

A method to "aid in treating" or to "aid in preventing" a disease or condition refers to a method that, together with additional actions, results in the treatment or prevention of the disease or condition.

Therapeutic Compositions and Kits

The oil palms include two species of the Arecaceae (palm) family, *Elaeis guineensis* (native to West Africa) and *Elaeis oleifera* (native to Central and South America). Most commonly used in commercial agriculture in the production of palm oil, mature trees grow to 20 m tall. The fruit takes five to six months to mature from pollination and comprises an oily, fleshy outer layer (pericarp) with a single seed (kernel). The oil palm does not produce offshoots and propagation is by sowing seeds. A cluster of fruit can weigh 40-50 kg.

Palm fruit extract can be prepared, for example, according to methods described by Sambanthamurthi et al., U.S. Pat. No. 7,387,802, incorporated by reference herein. In an exemplary embodiment of such methods, phytochemicals are extracted from a vegetation liquor derived from oil palm fruit in that an aqueous fraction or a concentrated aqueous fraction or a residue containing the phytochemicals is separated and recovered from the vegetation liquor, the separation removing in one or more steps substantially all oleaginous parts, substantially all undissolved solids, substantially all colloidal particles, and substantially all molecules above, for example, 41,000 Daltons in molecular weight. In preparing the palm fruit extract, some or substantially all of the water content of the aqueous fraction is removed to give a concentrated aqueous fraction or residue. The process can include obtaining a colloidal fraction and an aqueous fraction from the vegetation liquor by contacting the liquor with a material that adsorbs the oleaginous parts and filtering out the undissolved solids to give an essentially colloidal aqueous substance, and separating the substance into two fractions by one or more membrane filtrations, giving as retentate the colloidal fraction containing substantially all the colloidal particles and containing substantially all solutes having molecular weight greater than, for example, 41,000 Daltons, and giving as permeate a substantially clear aqueous fraction (i.e., palm fruit juice) containing solutes substantially all of which are below 41,000 Daltons in molecular weight. Centrifugation also can be used to remove colloidal particles from the vegetation liquor.

The composition of palm fruit juice has been described (Sambanthamurthi R, Tan Y A, Sundram K et al. (2011), Oil palm vegetation liquor: a new source of phenolic bioactives, Brit J Nutr 106, 1655-1663); this reference is incorporated by reference herein. Palm fruit juice total solids are composed mainly of carbohydrate (65%, mainly sucrose and fiber), protein (12%), ash (20%), and oil palm phenolics (~3.5%). For any selected extract the phenolic content can be measured as gallic acid equivalents (GAE) by spectrophotometric assay (Slinkard K, Singleton V L (1977) Total phenol analysis: automation and comparison with manual methods, Am J Enol Vitic 28, 49-55).

The water-soluble extract of the vegetation liquor from the palm oil milling process (referred to herein as "palm fruit juice") comprises phenolic compounds ("phenolics"). The phenolics found in palm fruit juice include, but are not limited to cinnamate and benzoate derivatives such as vanillic acid, chlorogenic acid, catechin, caffeic acid, protocatechuic acid, gentisic acid, 4-hydroxybenzoate, coumaric acid, ferulic acid, p-hydroxybenzoic acid, caffeoylshikimic isomers, and rutin hydrate. The detailed composition of oil palm phenolics has been described (see Sambanthamurthi et al. (2011)).

In certain embodiments, the composition may comprise sugars from the palm fruit juice. In certain embodiments, the sugars may include sucrose, fructose or glucose. In some embodiments the composition may comprise a combination of sugars, including a combination of sucrose, fructose and/or glucose. In other embodiments, the composition includes other sugars from the palm fruit juice.

A palm fruit juice-containing composition may be formulated in any conventional manner. While it is possible for the palm fruit juice-containing formula to be administered as the raw liquid, it may also be presented as a nutritional fruit juice or as a pharmaceutical formulation. Natural drinks or pharmaceutical formulations according to the present invention comprise the palm fruit juice-containing complex alone or a pharmaceutically acceptable salt thereof, together with one or more pharmaceutically acceptable carriers or excipients and optionally other therapeutic agents. The carrier(s) must be acceptable in the sense of being compatible with the other ingredients of the formula and not deleterious to the recipient thereof. In some embodiments, instead of natural phenolics, the compositions contain synthetic versions of the phenolics present in palm fruit juice.

The nutraceutical or pharmaceutical formulations described herein may include one or more other medicinal agents, pharmaceutical agents, carriers, adjuvants, and/or diluents. For example, a source of palm fruit juice may be combined with other active agents for the treatment of diabetes and other diseases and/or disorders described herein. Suitable oral antidiabetic agents include sulfonylureas, meglitinides, biguanides, thiazolidinediones, and α-glucosidase inhibitors.

Examples of carriers or recipients for oral administration include cornstarch, lactose, magnesium stearate, microcrystalline cellulose and stearic acid, povidone, dibasic calcium phosphate and sodium starch glycolate. Any carrier suitable for the desired administration route is contemplated by the present invention.

The compositions of the present invention may be contained in a solid dosage form (e.g., a pill, capsule, or tablet), a semi-solid dosage form or a liquid dosage form, each containing a predetermined amount of active ingredient. In certain embodiments, a solid dosage form is coated for ease of swallowing. The compositions of the present invention may be in the form of a powder or granules; or as a solution or suspension. For oral administration, fine powders or granules may contain diluting, dispersing, and or surface active agents and may be present in a solution or suspension in water or syrup, capsules or sachets in the dry state, in a nonaqueous solution or suspension wherein suspending agents may be included, or in tablets wherein binders and lubricants may be included. Components may be added such as flavoring, preservative, suspending, thickening or emulsifying agents.

Oral delivery methods are often limited by chemical and physical barriers imposed by the body, such as the varying pH in the gastrointestinal tract, exposure to enzymes, and the impermeability of the gastrointestinal membranes. Methods of the present invention for orally administering the nutritional supplement or pharmaceutical formulation may also include the co-administration of adjuvants with the compositions of the present invention. For example, nonionic surfactants such as polyoxyethylene oleyl ether and n-hexadecyl polyethylene ether can be administered with or incorporated into the formulations of the present invention to increase artificially the permeability of the intestinal walls. Other methods include the co-administration of enzymatic inhibitors with the formulations of the present invention. The active ingredients may also be present as a bolus or paste or may be contained within liposomes and emulsions.

Formulations for rectal administration may be presented as a suppository or enema.

When administered in the form of an aqueous liquid solution, the formulation will contain the source of palm fruit juice and water. Optional components in liquid solution include suitable solvents, buffering agents, sweeteners, anti-microbial preservatives, flavoring agents, other fruit juices, and mixtures thereof. A component of the formulation may serve more than one function. For example, a suitable buffering agent may also act as a flavoring agent as well as a sweetener.

Suitable solvents in the liquid solution used in the present invention include, for example, sorbitol, glycerin, propylene glycol, and water. A mixture of two or more solvents may optionally be used. The solvent or solvent system is typically present in an amount of from about 1% to about 90% by weight of the total liquid formulation.

Suitable buffering agents include, for example, citric acid, sodium citrate, phosphoric acid, potassium phosphate, and various other acids and salts. A mixture of two or more buffering agents may optionally be used. The buffering agent or mixtures thereof are typically present in an amount of from about 0.001 wt. % to about 4 wt. %.

Suitable sweeteners include, for example, saccharin sodium, sucrose, and mannitol. A mixture of two or more sweeteners may optionally be used. The sweetener or mixtures thereof are typically present in an amount of from about 0.001 wt. % to about 70 wt. %.

Suitable anti-microbial preservatives include, for example, methylparaben, propylparaben, sodium benzoate, and benzalkonium chloride. A mixture of two or more preservatives may optionally be used. The preservative or mixtures thereof are typically present in an amount of from about 0.0001 wt. % to about 2 wt. %.

Suitable flavoring agents may be used to the liquid solution a cherry flavor, cotton candy flavor, or other suitable flavor to make the solution easier for a patient to ingest. The flavoring agent or mixtures thereof are typically present in an amount of from about 0.0001 wt. % to about 5 wt. %.

In some embodiments, the extract is a reconstitutable concentrate or powder composition that, when reconstituted with, for example, water, milk, fruit juice or some other similar liquid will provide a drink, which may be used to provide an anti-hyperglycemic activity to a subject in need thereof. The concentrate or powdered composition and drink prepared therefrom are especially useful as an enterally administered component in a program of diabetes management which utilizes a number of carefully designed products in various forms, i.e., in shake, soup, fruit drink, snack bar and other solid forms such as tablets, gel caps, and the like, which can be mixed and matched over a period to provide more attractive and, therefore, more effective support to a patient, particularly those in extended care situations.

In addition to drinks, the extracts of the present invention may be used in foodstuffs. Such extracts may be combined with any other foodstuff, for example, water-soluble foodstuffs containing the extracts of this invention may be used. Grain flour fortified with the compounds of this invention may be used in foodstuffs, such as baked goods, cereals, pastas and soups. Advantageously, such foodstuffs may be included in low fat, low cholesterol or otherwise restricted dietary regimens.

Nutraceuticals may include nutritional drinks, diet drinks as well as sports herbal and other fortified beverages. In addition to the purified extract, the nutraceutical or foodstuff also may contain a variety of other beneficial components including but not limited to essential fatty acids, vitamins and minerals. These components should be well known to those of skill in the art, however, without being bound to any particularly formulations or content the present section provides a brief discussion of components that could form part of the food supplements of the present invention. Additional disclosure describing the contents and production of nutritional supplements may be found in e.g., U.S. Pat. Nos. 5,902,797; 5,834,048; 5,817,350; 5,792,461;

5,707,657 and 5,656,312, each of which is expressly incorporated herein by reference. Essential fatty acids such as γ-linolenic acid (ω-3) and linoleic acid (ω-6) may be added to the food supplements of the present invention. Essential fatty acids are involved in cardiovascular health as well as in support of the immune system. An imbalance in these essential fatty acids can lead to poor cholesterol metabolism.

The minerals zinc and copper are both involved in cardiovascular health, and should be provided in a ratio of 5:1 zinc:copper. An imbalance between these two minerals can cause an antagonistic effect of zinc on copper. This effect can interfere with the body's ability to use copper for supporting cardiovascular health. Too much zinc relative to copper can also interfere with the body's ability to manufacture SOD (superoxide dismutase), an important heart-protective enzyme. Also, a proper zinc:copper ratio is required to achieve a proper balance of HDL to LDL Zinc intake in the typical American man's diet is only 33 to 75 percent of RDA as such dietary supplements that include zinc are contemplated.

Selenium and iodide also have a ratio at which they function most effectively, which is the ratio of selenium to iodide of about 2:1. These minerals affect thyroid function, and therefore also have the resulting effects on metabolism caused by changes in thyroid function. Imbalanced thyroid function can put undue stress on the body that will result in malabsorption of nutrients from food. This, in turn, can retard growth and development.

Pyridoxine, folate and cobalamin also have a ratio at which they function most effectively in the prevention of vascular disorders. The optimal ratio of pyridoxine (vitamin $B_6$) to folate to cobalamin (vitamin $B_{12}$) is about 100:4:1, respectively. These vitamins affect cardiovascular function through their abilities to reduce the levels of the potentially toxic amino acid homocysteine. This ratio recognizes the imbalanced and inadequate levels of these vitamins consumed by individuals at risk of heart disease from their diet.

In addition, vitamin C, vitamin $B_1$ (thiamin), and vitamin E also can be provided. Vitamin C requirements are increased in smokers and cigarette smoking is a major contributor to lung cancer. Vitamin $B_1$ plays an essential role in energy transformation. Thiamin diphosphate (TDP) is a coenzyme necessary for the conversion of carbohydrates to energy. Since U.S. men currently consume about 45% of their total calories from carbohydrates, vitamin $B_1$ optimization in the diet is desirable.

Along with vitamin $B_6$, and vitamin $B_{12}$, folic acid supplementation help modulate blood levels of homocysteine and as such will be useful components in the dietary supplement formulations of the present invention. Vitamin D (calciferol) is essential for formation of the skeleton and for mineral homeostasis. Without vitamin D, the small intestine cannot absorb adequate calcium regardless of how much calcium is available for absorption. Thus, vitamin D is indicated as a component of a nutritional supplement to help build strong bones.

The role of manganese in driving metalloenzyme manganese-superoxide dismutase (Mn-SOD) has been clearly identified, along with a similar role in other metalloenzyme systems (glutamine synthetase, arginase, and pyruvate carboxylase). Numerous enzyme systems have also been shown to undergo manganese activation, even though they are not manganese metalloenzymes. The manganese-SOD connection may be of special clinical importance, since this form of the metalloenzyme appears to be the sole operative form within the cell's mitochondrial membranes, and thus may play a unique role in protection of the mitochondria and assurance of the body's oxidative energy production system. The inclusion of manganese in a dietary supplement would be desirable.

Additional micronutrients that may be included in the supplements include but are not limited to the vitamins such as vitamin A, vitamin C, vitamin E, riboflavin, niacin, niacinamide, pantothenic acid, pyridoxine, cobalamin, biotin, inositol, choline bitartrate, betaine, and vitamin K and minerals such as molybdenum, chromium and potassium.

In addition other flavorings and additives well known to those of skill in the art also may be added to the formulations to make them more palatable. For example, formulations may contain ginger, boswellia, fruit flavoring, coloring, preservatives and the like.

When ingested in a solid form, the nutraceutical composition described herein may additionally contain a solid carrier such as a gelatin or an adjuvant. When administered in liquid form, a liquid carrier such as water, petroleum, oils of animal or plant origin such as peanut oil, mineral oil, soybean oil, or sesame oil, or synthetic oils may be added. The nutraceutical composition described herein may also contain stabilizers, preservatives, buffers, antioxidants, or other additives known to those of skill in the art.

In some embodiments provided herein is a kit for treating or preventing mitochondrial dysfunction, mtDNA damage and/or genomic DNA damage in a subject comprising a composition described herein. For example, in some embodiments the kit contains a composition that includes phenolics, such as cinnamate, caffeoylshikimic isomers, and/or benzoate. Such compositions can be derived from natural sources (e.g., from palm fruit juice) or can be made synthetically. In some embodiments composition contains an extract from the vegetation liquor of the palm oil milling process.

In some embodiments the kit also includes an NRTI. Examples of NRTIs include, but are not limited to, zidovudine (3'-azido-3'-deoxythymidine, or AZT), didanosine, zalcitabine, stavudine, lamivudine, abacavir, emtricitabine, entecavir, apricitabine, tenofovir, adefovir, efavirenz, nevirapine, delavirdine, etavirine, and rilpvirine. In some embodiments the NRTI is AZT. In some embodiments the kit also includes an antitubercular drug. Examples of antitubercular drugs include, but are not limited to, isoniazid (INH), rifampicin (also known as rifampin in the United States), pyrazinamide, ethambutol; aminoglycosides: e g, amikacin (AMK), kanamycin (KM); polypeptides: e.g., capreomycin, viomycin, enviomycin; fluoroquinolones: e.g., ciprofloxacin (CIP), levofloxacin, moxifloxacin (MXF); thioamides: e.g. ethionamide, prothionamide, cycloserine: e.g., closerin Terizidone: In some embodiments the antitubercular drug is INH Therapeutic Methods Disclosed herein are methods of treating and/or preventing, as well as methods to aid in treating or preventing, mitochondrial dysfunction and/or mtDNA damage. Such methods are useful, for example, in the treatment of age-related and mitochondrial diseases. In certain embodiments the method includes the step of administering a composition described herein (e.g., a composition comprising palm fruit juice and/or synthetic phenolics found in palm fruit juice) to a subject (e.g., a subject in need thereof).

In some embodiments, the subject has HIV and/or AIDS. In some embodiments the subject has been administered an agent that increases the risk of or causes mitochondrial dysfunction and/or mtDNA damage. For example, in some embodiments, the subject has been administered an NRTI. Examples of NRTIs include, but are not limited to, zidovudine (3'-azido-3'-deoxythymidine, or AZT), didanosine, zalcitabine, stavudine, lamivudine, abacavir, emtricitabine, entecavir, apricitabine, tenofovir, adefovir, efavirenz, nevirapine, delavirdine, etavirine, and rilpvirine. In some embodiments the subject has been administered AZT.

In some embodiments the subject has or is suspected of having a mitochondrial DNA mutation. In certain embodiments the method further includes the step of determining whether the subject has a mtDNA mutation.

Any method of identifying mtDNA mutations known in the art can be used to determine whether the subject has a mtDNA mutation in a method of the invention. Thus, in certain embodiments, the determining step includes performing a nucleic acid amplification assay and/or performing a nucleic acid sequencing assay. Examples of nucleic acid amplification processes include, but are not limited to, polymerase chain reaction (PCR), LATE-PCR a non-symmetric PCR method of amplification, ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) and/or rolling circle amplification (RCA). Nucleic acid sequencing processes include, but are not limited to chain termination sequencing, sequencing by ligation, sequencing by synthesis, pyrosequencing, ion semiconductor sequencing, single-molecule real-time sequencing, 454 sequencing, and/or Dilute-'N'-Go sequencing.

As described herein, the LATE-PCR/Lights-On/Lights-Off/PCR-Perfect technology disclosed herein can be used to detect and quantify the amount of DNA damage in virtually any set of sequences in mitochondrial genomes analyzed in multiplexed, closed-tube reactions. See also WO 2012/075230, hereby incorporated by reference, for description of this methodology. Generally, this method includes using LATE-PCR at the near-digital level to generate single stranded amplicons, which allows one to test for mutational events by scanning relatively long stretches of mtDNA using Lights-On/Lights-Off probes. Briefly, Lights-On/Lights-Off probes are combinations of two types of probes. The first type, the so-called Lights-On probe, has a fluorophore and a quencher attached to either end of the probe. When bound to its target, the probe fluoresces. The second type of probe, the Lights-Off probe, has only a quencher. When the "off probe" binds its target, the quencher is positioned next to the fluorophore on the corresponding Lights-On probe, quenching any fluorescence from the Lights-On probe. In this way a target sequence up to several hundred nucleotides long can be coated with sets of probes in a single fluorescent color. Each probe binds at a specific temperature, so that as each probe melts off its target, a pattern of fluorescence is produced. Any change in the underlying sequence will be displayed as a shift in temperature at which a probe will bind, and thus change the fluorescence signature. In this way Lights-On/Lights-Off probes can rapidly detect mutations.

In some embodiments, described herein are therapeutic methods of treating and/or preventing a mitochondrial disease. Mitochondrial diseases include, but are not limited to, mitochondrial myopathy, diabetes mellitus and deafness (DAD), Leber's hereditary optic neuropathy (LHON), Leigh syndrome, neuropathy, ataxia, retinitis pigmentosa and petosis (NARP), myoclonic epilepsy with ragged red fibers (MERRF), myoneurogenic gastrointestinal encephalopathy (MNGIE), mitochondrial myopathy, encephalomyopathy, lactic acidosis, stroke-like symptoms (MELAS), Kearns-Sayre syndrome (KSS), chronic progressive external opthalmoplegia (CPEO) and/or mtDNA depletion.

In some embodiments, provided herein are methods of treating and/or preventing an age-related disease. Age-related diseases include, but are not limited to, Alzheimer's disease, amyotrophic lateral sclerosis, arthritis, atherosclerosis, cachexia, cancer, cardiac hypertrophy, cardiac failure, cardiac hypertrophy, cardiovascular disease, cataracts, colitis, chronic obstructive pulmonary disease, dementia, diabetes mellitus, frailty, heart disease, hepatic steatosis, high blood cholesterol, high blood pressure, Huntington's disease, hyperglycemia, hypertension, infertility, inflammatory bowel disease, insulin resistance disorder, lethargy, metabolic syndrome, muscular dystrophy, multiple sclerosis, neuropathy, nephropathy, obesity, osteoporosis, Parkinson's disease, psoriasis, retinal degeneration, sarcopenia, sleep disorders, sepsis and/or stroke.

In some embodiments, provided herein are methods of treating HIV and/or AIDS. In certain embodiments the method includes the step of administering a composition described herein (e.g., a composition comprising palm fruit juice and/or synthetic phenolics found in palm fruit juice) to a subject (e.g., a subject in need thereof). In some embodiments the method also includes administering a NRTI to the subject. Examples of NRTIs include, but are not limited to, zidovudine (3'-azido-3'-deoxythymidine, or AZT), didanosine, zalcitabine, stavudine, lamivudine, abacavir, emtricitabine, entecavir, apricitabine, tenofovir, adefovir, efavirenz, nevirapine, delavirdine, etavirine, and rilpvirine. In some embodiments the NRTI is AZT.

Disclosed herein are methods of treating and/or preventing genomic DNA damage in a subject. In certain embodiments the method includes the step of administering a composition described herein (e.g., a composition comprising palm fruit juice and/or synthetic phenolics found in palm fruit juice) to a subject (e.g., a subject in need thereof).

In some embodiments the treated subject has or is predisposed to cancer. The methods described herein can be used to treat any form of cancer. In some embodiments, when used for treating cancer, the methods provided herein comprise administering a composition described herein in conjunction with one or more chemotherapeutic agents. Examples of such chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

The methods described herein may be used to treat any cancerous or pre-cancerous tumor. Cancers that may be treated, prevented or diagnosed by methods and compositions described herein include, but are not limited to, cancer cells from the bladder, blood, bone, bone marrow, brain, breast, colon, esophagus, gastrointestinal tract, gum, head, kidney, liver, lung, nasopharynx, neck, ovary, prostate, skin, stomach, testis, tongue, or uterus. In addition, the cancer may specifically be of the following histological types, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the subject to be treated has been exposed to a condition that increases the likelihood of genomic DNA damage. For example, in some embodiments the subject has been exposed to elevated levels of ionizing radiation (e.g., the subject has undergone radiation therapy) and/or the subject has been exposed to or consumed a mutagen. Examples of such mutagens include, but are not limited to, acetaldehyde, aflatoxins, 4-aminobiphenyl, areca nut, aristolochic acid, arsenic, asbestos, azathioprine, benzene, benzidine, benzo[a]pyrene, beryllium, betel quid, bis (chloromethyl)ether, busulfan, 1,3-butadiene, cadmium, chlorambucil, chlornaphazine, chromium (VI) compounds, clonorchis sinensis, cyclophosphamide, cyclosporine, diethylstilbestrol, erionite, ethylene oxide, etoposide, formaldehyde, ionizing radiation, melphalan, methoxsalen, 4,4'-methylenebis(chloroaniline), MOPP, 2-naphthylamine, neutron radiation, nickel compounds, N'-nitrosonornicotine, 4-(N-nitrosomethylamino)-1-(3-pyridyl)-1-butanone, 3,4,5, 3',4'-pentachlorobiphenyl, 2,3,4,7,8-pentachlorodibenzofuran, phenacetin, phosphorus-32, plutonium, radioiodines, radionuclides, radium-224, radium-226, radium-228, radon-222, semustine, shale oils, sulfur mustard, 2,3,7,8-tetrachlorodibenzo-para-dioxin, thiotepa, thorium-232, ortho-toluidine, treosulfan and vinyl chloride.

In some embodiments the subject has or is suspected of having a genomic DNA mutation. In certain embodiments the method further includes the step of determining whether the subject has a genomic DNA mutation.

Any method of identifying genomic DNA mutations known in the art can be used to determine whether the subject has a mtDNA mutation. Thus, in certain embodiments, the determining step includes performing a nucleic acid amplification assay and/or performing a nucleic acid sequencing assay. In some embodiments the determining step is performed using LATE-PCR/Lights-On/Lights-Off/PCR-Perfect technology. Examples of nucleic acid amplification processes include, but are not limited to, polymerase chain reaction (PCR), LATE-PCR, ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) and/or rolling circle amplification (RCA). Nucleic acid sequencing processes include, but are not limited to chain termination sequencing, sequencing by ligation, sequencing by synthesis, pyrosequencing, ion semiconductor sequencing, single-molecule real-time sequencing, 454 sequencing, and/or Dilute-'N'-Go sequencing.

As described above, in certain embodiments, the methods described herein include administering a composition described herein in conjunction with a second therapeutic agent to the subject. Conjunctive therapy includes sequential, simultaneous and separate, or co-administration of the active compound in a way that the therapeutic effects of the first agent administered have not entirely disappeared when the subsequent agent is administered. In certain embodiments, the second agent may be co-formulated with the first agent or be formulated in a separate nutraceutical or pharmaceutical composition.

Actual dosage levels of the active ingredients in the pharmaceutical and nutraceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the nutraceutical or pharmaceutical composition required. For example, the physician or veterinarian could prescribe and/or administer doses of the compounds of the invention employed in the nutraceutical or pharmaceutical composition at levels lower than that required in order to achieve the desired therapeutic effect and gradually increase the dosage until the desired effect is achieved.

The invention now being generally described, it will be more readily understood by reference to the following examples, which are included merely for purposes of illustration of certain aspects and embodiments of the present invention, and are not intended to limit the invention.

EXAMPLES

Example 1: PFJ Reduces the Number of Mitochondrial Mutations Caused by AZT

A thirty day experiment was conducted using the HepG2 liver carcinoma cell line (ATCC, Manassas, Va.). The experiment included analysis of non-treated, AZT-treated, PFJ-treated, and AZT and PFJ-treated cultures. Each condition was tested in triplicate.

The cells were grown in Eagle's Minimum Essential Medium (ATCC Manassas, Va.). The media were supplemented with 10% fetal bovine serum (BioWest) and antibiotics containing 50 units/mL penicillin G, 50 units/mL streptomycin, and 0.25 μg amphotericin B (HyClone Antibiotic/Antimycotic Solution 100×). The treated replicates were given 7 μM AZT (Sigma, St. Louis, Mo.), 25 μg/mL PFJ, or 7 μM AZT plus 25 μg/mL PFJ. The cells were grown in 75 $cm^3$ tissue culture flasks (Sigma, St. Louis, Mo.) at 37° C. and 5% $CO_2$. The media were changed every other day. The cells were passaged by trypsinization as per ATCC's instructions.

The DNA from HepG2 cells was extracted by placing 1 μl of cell suspension (on average 1000 cells) into 14 μl volume of a lysis buffer containing 100 μg/ml proteinase K, 10 mM Tris-Cl pH 8.3, and 5 μM SDS (sodium-dodecyl-sulfate) and heating to 50° C. for 2 hours followed by 95° C. for 15 minutes. The samples were then stored at −20° C.

For analysis of mutational load, DNA samples were diluted to the near-digital (5-4 copies) level or below and amplified in replicates in 96-well plate using a multiplex LATE-PCR assay consisting of three pairs of LATE-PCR primers that targeted three regions of the mitochondrial genome: cytochrome c oxidase subunit 2 (CO2), NADH dehydrogenase, subunit 1 (ND1), and the hyper variable 2 (HV2) region of the D-Loop. All of these regions are known to have sequence changes that are related to human disease.

The resulting single-stranded amplicons were 586 base pairs (CO2), 604 base pairs (ND1) and 588 base pairs (HV2) in length. At the end of the amplification reaction, these single-stranded products were simultaneously scanned for mutations using sets of Light-On/Lights-Off probes of a different color for each amplicon which were included in the original amplification reaction mixture (CO2, Cal Red 610; HV2, Quasar 670, ND1, Cal Orange 560; fluorophores were obtained from Biosearch Technologies, Novato Calif.). The probes hybridized at temperatures below the primer annealing temperature and did not interfere with amplification. Each Lights-On probe was labeled with a quencher and a fluorophore and generated a fluorescent signal when hybridized to its target sequence in the absence of an adjacent Lights-Off probe. Each Lights-Off probe was labeled with only a quencher and was designed to extinguish the signal from its paired Lights-On probe when hybridized to the adjacent target sequence at a lower temperature. Melting of the complete set of Lights-On/Lights-Off probes hybridized along the length of their target amplicon generated a fluorescent signature that was unique for the sequence of each amplicon. Any change from a reference normal fluorescent signature generated from bulk samples (1000 targets or more) indicated the presence of a mutation. Mutations could be single or multiple nucleotide changes, deletions, or insertions anywhere in the target sequence. The fluorescent color and temperature of the change relative to the normal reference signature indicated the presence and approximate location of the mutation.

Reaction components and conditions were as follows:

```
Limiting Primer:
                                              (SEQ ID NO: 1)
5'-AAAGCGGTGTGTGTGTGCTGGGTAGGAT Excess Primer:
                                              (SEQ ID NO: 2)
5'-ACTTCAGGGTCATAAAGCCTAAATAGC CO2 Primers
Limiting Primer:
                                              (SEQ ID NO: 3)
5'-AATAGAGGGGGTAGAGGGGGTGCTATAGGGT Excess Primer:
                                              (SEQ ID NO: 4)
5'-TCCTTATCTGCTTCCTAGTCCTGTATGC ND1 Primers
Limiting Primer:
                                              (SEQ ID NO: 5)
5'-AACATAAGAACAGGGAGGTTAGAAGTAGGGTCTTGGT Excess Primer:
                                              (SEQ ID NO: 6)
5'-CGCCCCGACCTTAGCTCT Target: HV2
                                              (SEQ ID NO: 7)
5'GCTCGCCACACACACACGACCCATCCTACCCGCCCCCAACATAACTA

CTCTAATCATCATACCCTCACCCTCCCCTTTTATTACACAATCAACCCC

CCACTGACAATTTTCACGTATGGCGGTTTTCTATTTTAAACTTTAGACC

AATCCGACCACAATCCCAAGAAACAAAAACCCCAAACCGTCTCTACACA

AATTCACGACACCGGTCTTCGCCCCCTCCCCCCCAAACCACCTTTAAAA

AACAATACTACAGACACACCTTTCACCGACACGTCTGTAAGTTAACAAT

AATAATACAGGATGTTCGTAATTAATTAATTGTGTGAAATCATTCATAC

AAGCGGACATTATAACTTGCATCCACGCTATTTATTATCCTACTCCGTC

CTTAGTTTCTGTCTATGACGCTGTATCCCACGAGGCCGAGGTCGCAGAG

CGTTACGATAGCGCACGTATGGGGGGTCTGCTTTTATGGTTTACGTACC

TCTCGAGGGCACTCACCAATTATCCCACTATCTGGACACTAGGTAGCAC

TACAGAATAAATTCCCCTTGCACACCCGATAAATCCGAAATACTGGGAC

TTCA

Target: CO2
                                              (SEQ ID NO: 8)
5'CCCGAGATCTCCCCCATCTCCCCCACGATATCCCATTTATGCCCGGG

ATAAAGTTTCTAAAAATCCCCTTAATTAAGATCCTGCTACCCGTACTTT

GACACCAAACGAGGTGTCTAAAGTCTCGTAACTGGCATCATATGGGGGC

CAGCACATCGCCACTTTCACCAAACCAAATCTGCAGGCCCTTAACGTAG

ACAAAAATTCGGATTACACCCCTGTCGAGTACTCACGTTCTGCAGAACA

CTACATTAATAATATGCTTACCCCCGAAGTTAGCCCTCATGATGAGCTA

ACAGTTGCAGTTCCTCAGCGTCCAGCGGACCAAGATCCTTATTACCCCC

TTCATACATCCTCAACTTCTAATCAGGCGGCATCAGCCACATGAGCATC

CAAGTCATGGTAACCACCGGTTAACTAAACTACCATTCCCTCCCTAGCA

ACTGGAGCAGACAATACATTTCCTACGCATCCCTACCCTCCCGCTACTC

CTGATCCTACTACCGCCCGTCCTATCAAGTCTGCCAAAGATAAAGGACT

CGCAGACTCTACAATCATAATCAATCAAAACAACACTCACAATCCTTTT

CCCGTATGTCCTGATCCTTCGTCTATTCCT

Target: ND1
                                              (SEQ ID NO: 9)
5'AAGTATTCTTGTCCCTCCAATCTTCATCCCAGAACCACTGTTTTATA

CAACACATCTCAAGTCCCCTCTCACGCAGTATACAACAAGGATCCTTCT

AACATCACCACTCCCACAAATAATATTATTACAAACACATAAGCCGATA

CTTCTTATCCCGCTTCCCCGGACGCCGCATAAGCTACAACTTCGGACTC

TGATCAAGCCTGAGGGGAAGCCGTTCCAGCTTCCCCCAAGCCAACCAGA

GACGATCACACCTCTATTTAGTATAATACCGGTTCCCAGTACTACCGTC

CTCATTAGTCTCCACAAGAACACAACACTATTCCCACCTCTCCAATTTC

CTCGGTGAATAATCATTACAACTATCATCTTACTACCGATCCCACTGAA

GTATACTCTAACAAACCCGATGACGAGCGTCACGCGGCTAGTCCCGCAT

CAAACTCAAACTACGAGTGGGACTAGTCTCCTAACTCATTTGCCGATCC

GATCTCCACCGATCTTATTTATCCTCCGGATCCAACTCCAACTGGTCCC

CCAACCCATACCCCTCCCCCCAAGTATCATCTTCTCGCTACCACTCTCG

ATTCCAGCCCCGC

HV2 Probes
On 1:
                                              (SEQ ID NO: 10)
5'-Quasar 670-TGGTTAGGGTTCTTTATTTTGGGGTTCA-BHQ2

Off 1:
                                              (SEQ ID NO: 11)
5'-AATGTGAAATCTGCTTGGGCTGGT-BHQ2

On 2:
                                              (SEQ ID NO: 12)
5'-BHQ2-AATGGCAGAGATGTCTTTAAGTGCTGTTT-Quasar 670

Off 2:
                                              (SEQ ID NO: 13)
5'-BHQ2-GGCTAGGAGTTGGGGAGGGCGGGTT-C3

On 3:
                                              (SEQ ID NO: 14)
5'-BHQ2-AAATGTAATCGCGTTCATATCACCCAGTT-Quasar 670

Off 3:
                                              (SEQ ID NO: 15)
5'-BHQ2-ACGAGAGTACCCAACGCATGGAGAG-C3
```

-continued

On 4:
(SEQ ID NO: 16)
5'-Quasar 670-TAATTGAACATAGGTACGATAAATAATTA-BHQ2

Off 4:
(SEQ ID NO: 17)
5'-TTTAGTAAATGTGTTCACCTGTAAT-BHQ2

On 5:
(SEQ ID NO: 18)
5'-Quasar 670-AACTGGGTGAAAAGTGACTATGCGGACTT-BHQ2

Off 5:
(SEQ ID NO: 19)
5'-TGGGGGAAGTTTTTTCTTATTATGT-BHQ2

CO2 Probes
On 1:
(SEQ ID NO: 20)
5'-BHQ2-AAACTACTCGATTATCAACGTCAAGGATT-Cal Red 590

Off 1:
(SEQ ID NO: 21)
5'-BHQ2-GTCGCAGGACGCCTAGTTTTAGGAA-C3

On 2:
(SEQ ID NO: 22)
5'-BHQ2-AAAATGGGGAAGTTTGTATGAGTTGATT-Cal Red 590

Off 2:
(SEQ ID NO: 23)
5'-BHQ2-AGATAAGTTCGCTGTATTCGGTGT-C3

On 3:
(SEQ ID NO: 24)
5'-Cal Red 590-AAACGATTGGGGACTTTAATTGGGAGTTT-BHQ2

Off 3:
(SEQ ID NO: 25)
5'-AGACGTCTTATGTTGTAATTAT-BHQ2

On 4:
(SEQ ID NO: 26)
5'-Cal Red 590-TTTGTAAAGAATGCGTAGAGATAGGAGAA-BHQ2

Off 4:
(SEQ ID NO: 27)
5'-GAGGCATTGTTCACGTCGTTTGTTA-BHQ2

On 5a:
(SEQ ID NO: 28)
5'-BHQ2-TTTTTATACGTACGGCAATTACATCTGAA-Cal Red 590

Off 5a:
(SEQ ID NO: 29)
5'-BHQ2-TTTTTAAATTTAATATGGGGATAGC-C3

On 5b:
(SEQ ID NO: 30)
5'-BHQ2-AGTGACCATAATATACCTCCGGCT-Cal Red 590

Off 5b:
(SEQ ID NO: 31)
5'-BHQ2-TCGTATAGTGGTCAATGTGGTATGG-C3

ND1 Probes
On 1:
(SEQ ID NO: 32)
5'-Cal Orange 560-AAGTTCGGTTGGTTTTTGCTGGTGTGGTT-BHQ1

Off 1:
(SEQ ID NO: 33)
5'-TTCGGCAATGTCGAGGGGG-BHQ1

On 2:
(SEQ ID NO: 34)
5'-BHQ1-AATATGAAGAATAGAGCGAAGAGGCCTTT-Cal Orange 560

Off 2:
(SEQ ID NO: 35)
5'-BHQ1-GCGGCCTATTCCATGTTGACGCCTG-C3

On 3:
(SEQ ID NO: 36)
5'-BHQ1-TTAAGGTTGTAGTGATGGGGGTGTTTAAA-Cal Orange 560

Off 3:
(SEQ ID NO: 37)
5'-BHQ1-TTATAATAATCTTTGTGTTTTCGGC-C3

On 4:
(SEQ ID NO: 38)
5'-BHQ1-AATTGATCAAGGGGTTTGGTATAGGGATT-Cal Orange 560

Off 4:
(SEQ ID NO: 39)
5'-BHQ1-GGGAGGTTTATAGTAAAAGAGAGAT-C3

On 5:
(SEQ ID NO: 40)
5'-BHQ1-TTAGATAAACCATAGTATGTCCGAGGGAA-Cal Orange 560

Off 5:
(SEQ ID NO: 41)
5'-BHQ1-TCATGATTGCAGTAGTGGTAAGAGG-C3

A three carbon linker is denoted with $C_3$ while Black Hole Quenchers 1 and 2 are denoted by BHQ1 and BHQ2 (Biosearch Technologies, Novato Calif.). Underlined bases are those that are mismatched to the revised Cambridge Reference Sequence (rCRS).

LATE-PCR amplifications were carried out in a 25 µl volume consisting of 1×PCR buffer (Invitrogen, Carlsbad, Calif.), 3 mM $MgCl_2$, 250 nM dNTPs, 50 nM Limiting Primer, 1000 nM Excess Primer (HV2), 100 nM Limiting Primer, 1000 nM Excess Primer (CO2), 50 nM Limiting Primer, 1500 nM Excess Primer (ND1), 2.5 units of Platinum Taq DNA Polymerase (Invitrogen, Carlsbad, Calif.), 100 nM of the Lights-On probes, and 300 nM of the Lights-Off probes. Control reactions consisted of 10-20 replicate bulk samples containing 1000 mitochondrial DNA genomes. The thermal profile for the amplification reaction was as follows: 95° C./3 min for 1 cycle, followed by 95° C./5 s-65° C./45 s-72° C./90 s for 65 cycles, for bulk analysis and 75 cycles for low copy analysis, followed by a single cycle of 75° C. for 10 min and a single cycle of 25° C. for 10 min. The reaction products were characterized by the use of melt profile analysis. Fluorescent acquisition of the probe signals was carried out at each degree in a melt starting at 25° C. with 1° C. increments at 45 s intervals to 80° C. Fluorescent signatures were generated by plotting the negative first derivative of the raw fluorescent signals from the melting analysis relative to temperature as a function of temperature without any background signal subtraction or data normalization. Mutations were identified by comparing the shape of fluorescent signature from the test sample to the shape of the average fluorescent signature from the replicate bulk samples which served as a reference.

Figure 1B:
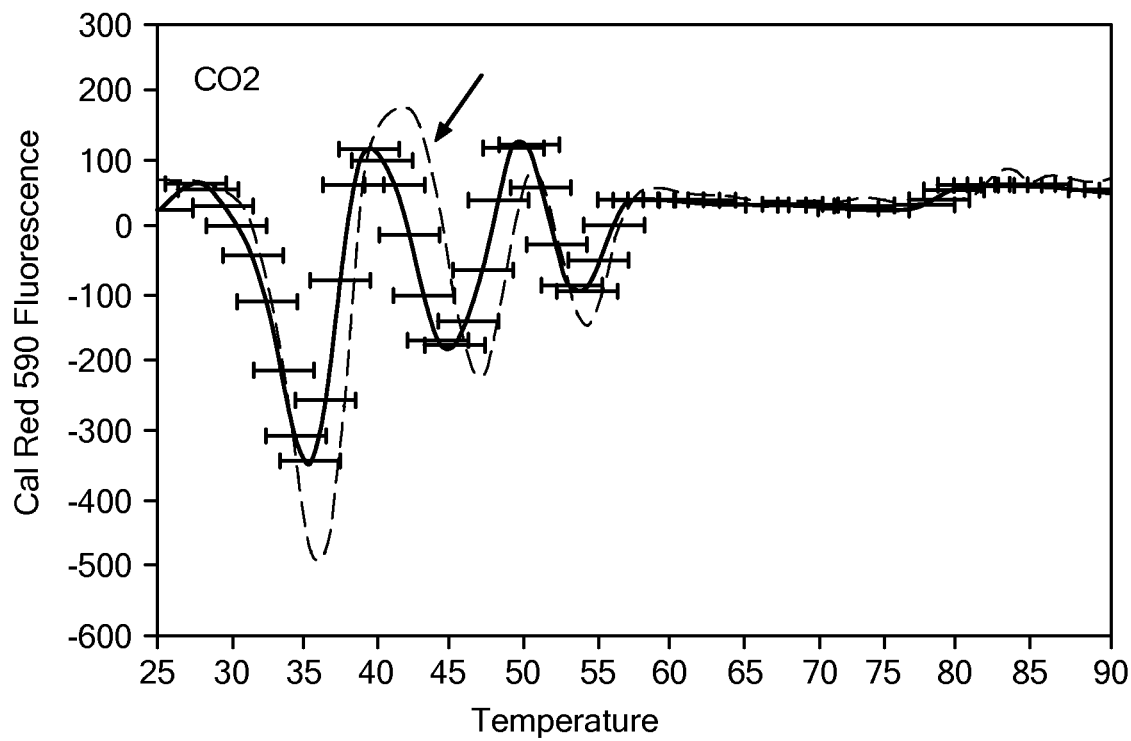
Figure 1C:
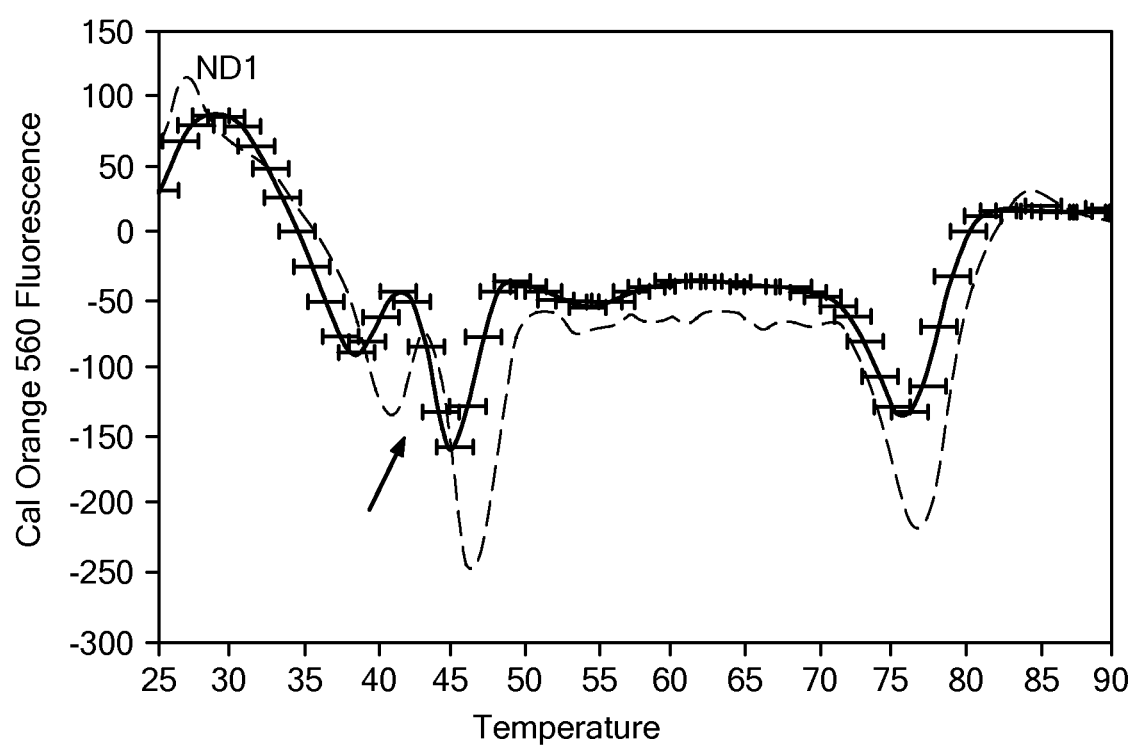

FIGS. 1A-1C show the fluorescent signature changes indicative of a mutation in the mitochondrial DNA for each of the three targets HV2, CO2, and ND1, respectively. The black line indicates the reference sequence and the gray line represents the shifted signature. Arrows indicate areas of difference and evidence of the mutation. Error bars represent three standard deviations from the mean reference.

Figure 2:
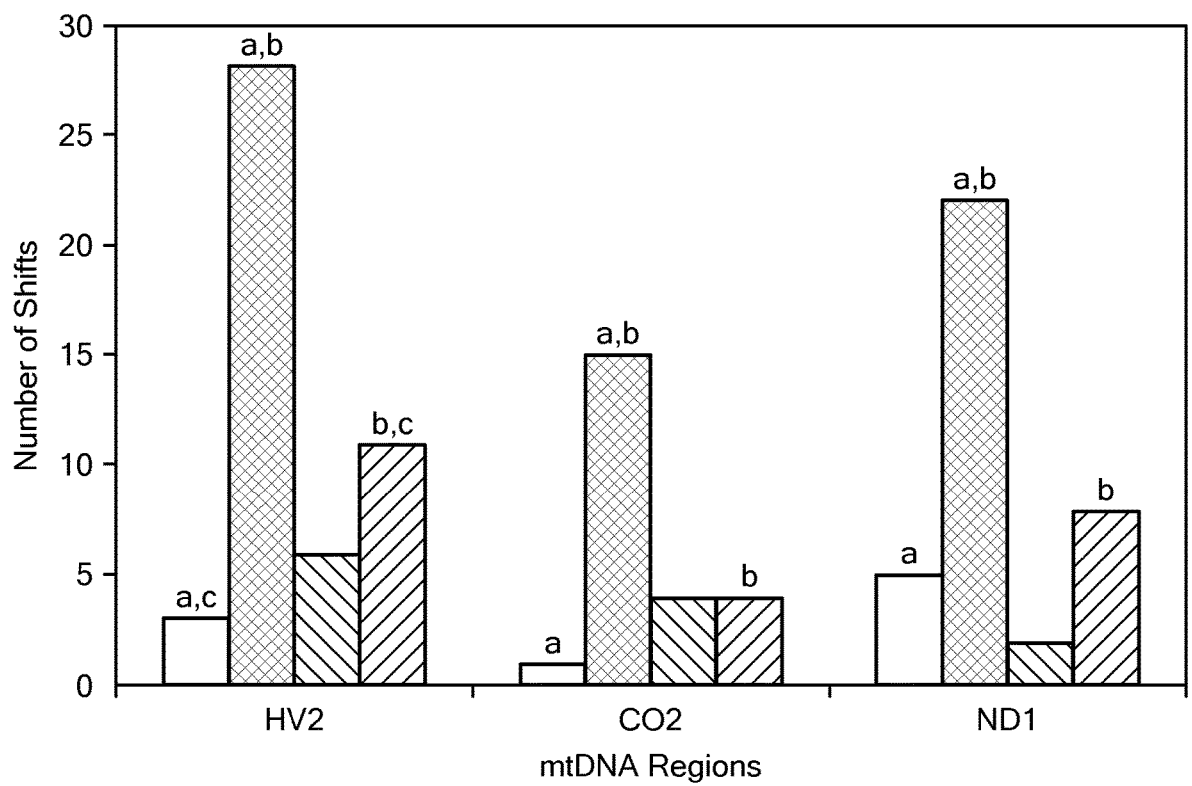
FIG. 2 shows the number of signature shifts that reflects mutations based on treatment (no treatment, AZT treatment, PFJ treatment, or both AZT and PFJ Treatment) for each of the mitochondrial genome targets (HV2, CO2, and ND1). White bars indicate the non-treated controls, the black bars indicate the AZT treatment, gray bars indicate the PFJ treatment, and the bars with diagonal lines indicate the AZT and PFJ treatment. Letters above the bars indicate significant differences ($p<0.05$) between treatments: A, control vs. AZT treatment; B, AZT treatment vs. AZT+PFJ treatment; C, control vs. AZT+PFJ treatment.

FIG. 2 shows the number of fluorescent signature changes indicative of mutations based on treatment (no treatment, AZT treatment, PFJ treatment, or both AZT and PFJ treatment) for each of the mitochondrial targets. Lower case letters indicate significant differences (p<0.05) between treatments. Unfilled bars indicate the non-treated controls, while the black bars indicate the AZT treatment, the gray bars indicate the PFJ treatment, and the bars with diagonal lines indicate the AZT and PFJ treatment.

Example 2: PFJ Reduces the Number of Mitochondrial Mutations Caused by INH

A liver carcinoma cell line (HepG2 cells, ATCC, Manassas, Va.) was grown for 30 days in the presence of either 88 µM INH (Sigma, St. Louis, Mo.) or 88 µM INH+50 µg/ml gallic acid equivalents (GAE) PFJ. A culture without these additives served as a non-treated control. Cells were grown in Eagle's Minimum Essential Medium (ATCC Manassas, Va.). The media were supplemented with 25 mM HEPES, 10% fetal bovine serum (BioWest), 50 units/mL Penicillin G, 50 units/mL Streptomycin, and 0.25 µg Amphotericin B (HyClone Antibiotic/Antimycotic Solution 100×) in 6-well plates at 37° C. and 5% $CO_2$. The media and additives were replenished every other day. The cells were passaged as per ATCC's instructions at an initial density of $1\times10^5$ cells/ml.

At the end of the culture period, each HepG2 culture was tripsinized, spun at 100×g for 15 min at 4° C. and resuspended in Dulbecco's phosphate buffer solution (Sigma, St. Louis, Mo.) at a concentration of $1\times10^3$ cells/ml. DNA from these cultures was extracted by placing 5 µl of cell suspension into 32.5 µl volume of a lysis buffer containing 100 µg/ml proteinase K, 10 mM Tris-Cl pH 8.3, and 5 µM SDS (sodium-dodecyl-sulfate) and heating to 50° C. for 2 hours followed by 95° C. for 15 minutes. The samples were then stored at −20° C.

DNA samples were diluted to the near-digital (5-4 copies) level or below and interrogated for fluorescent signatures changes indicative of mutations in replicates in a 96-well plate using the multiplex LATE-PCR/Lights On-Lights Off assay described in Example 1.

Figure 3:
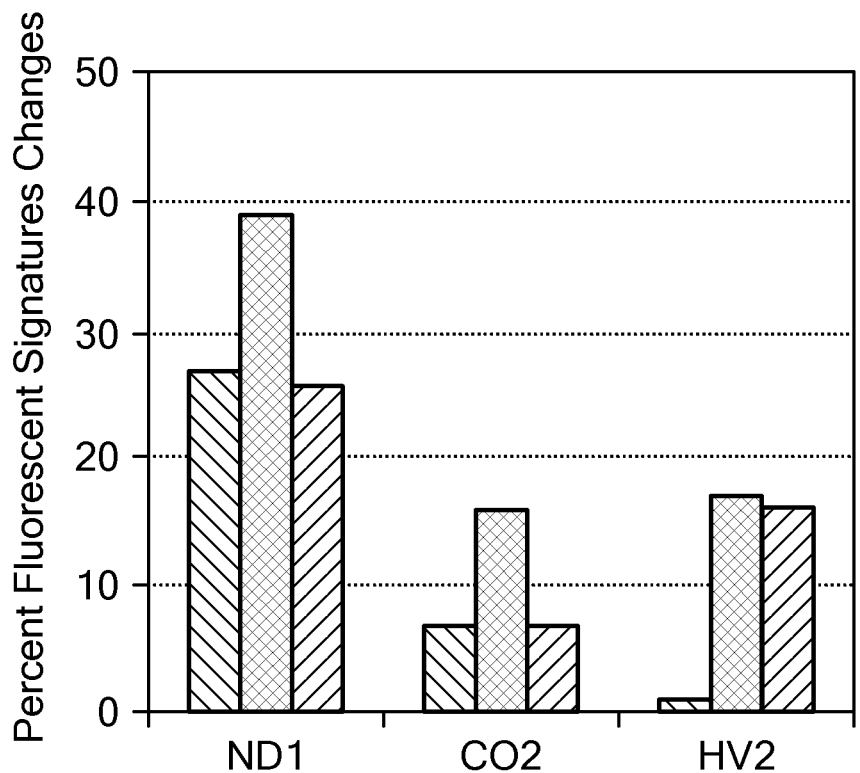
FIG. 3 shows the number of fluorescent signature changes indicative of mitochondrial DNA mutations based on treatment (no treatment, isoniazid (INH) treatment, both INH and PFJ Treatment) for three regions of the mitochondria genome (HV2, CO2, and ND1). The results indicate that INH treatment increases mtDNA mutational load and that PFJ treatment reduces the number of these mutations.

FIG. 3 shows the percent of fluorescent signature changes indicative of mitochondrial DNA mutations based on treatment (medium gray bars, no treatment; dark gray bars, INH treatment; light gray bars, INH and PFJ treatment) for each of the mitochondrial targets (medium gray bars, no treatment; dark gray bars, INH treatment; light gray bars, INH and PFJ treatment). The results indicate that INH treatment increases mtDNA mutational load and that co-treatment of the cells with IHN and PFJ reduces the number of INH-induced mutations.

Figure 4:
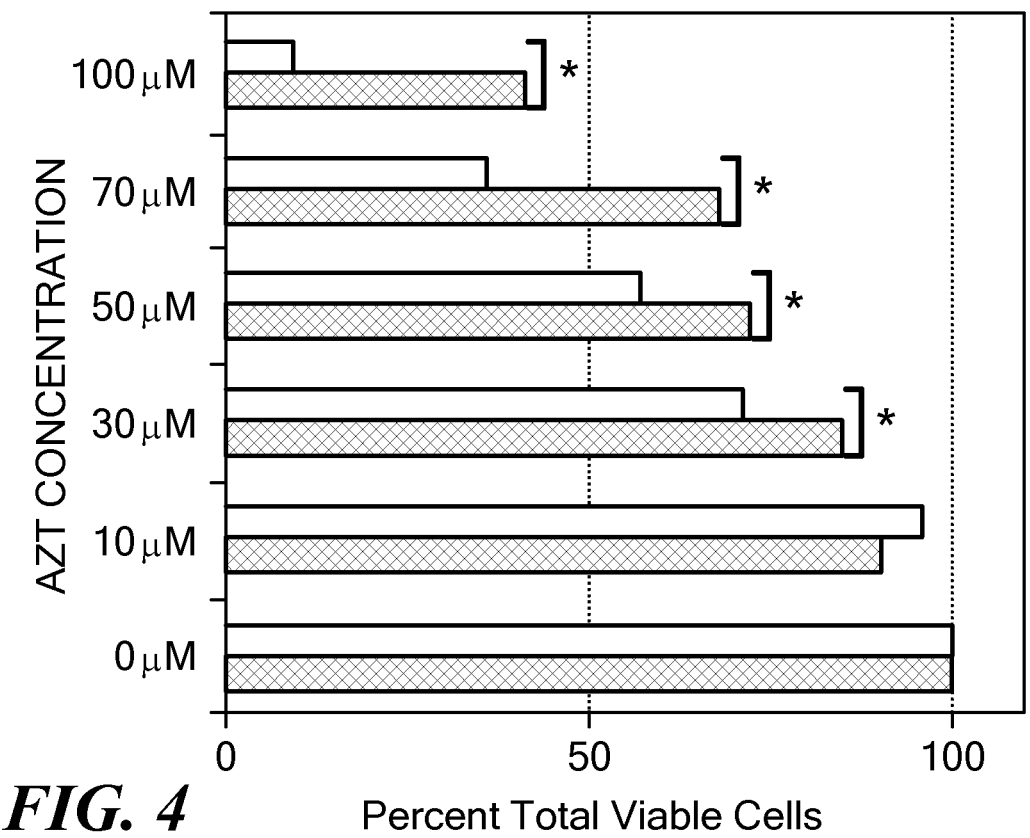
FIG. 4 shows the protective effects of PFJ treatment on dose-dependent AZT cytotoxicity in HepG2 cells.

Example 3: Protective Effects of PFJ Treatment on Dose-Dependent AZT Cytotoxicity in HepG2 Cells HepG2 cultures were set up with increasing concentrations of AZT (0 µM, 10 µM, 30 µM, 50 µM, 70 µM, 100 µM) in the presence or absence of 75 µg/ml GAE equivalents PFJ. Each culture was initially seeded with $1\times10^5$ cells/ml. Culture conditions were as described in Example 2. FIG. 4 shows the percent viable cells recovered after six days of culture (unfilled bars, cells treated with AZT; black bars, cells treated with AZT and PFJ). Asterisks show samples where the difference between the percent of recovered viable cells from the AZT and AZT/PFJ treated samples was statistically significant. The results illustrate the cytotoxic effect of increasing AZT concentrations and demonstrate the mitigating effect of PFJ treatment on AZT cytotoxicity.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method of treating or preventing mitochondrial dysfunction in a subject who has been administered a nucleoside reverse transcriptase inhibitor (NRTI) or isoniazid, the method comprising administering to the subject a composition containing a water soluble extract from a fruit of genus *Elaeis* or one or more phenolic compounds present in a water soluble extract from a fruit of genus *Elaeis*.

2. A method of treating or preventing mtDNA damage in a subject who has been administered a nucleoside reverse transcriptase inhibitor (NRTI) or isoniazid, the method comprising administering to the subject a composition comprising a water soluble extract from a fruit of genus *Elaeis* or one or more phenolic compounds present in a water soluble extract from a fruit of genus *Elaeis*.

3. The method of claim 1, further comprising administering an NRTI to the subject.

4. The method of claim 1, wherein the NRTI is 3'-azido-3'-deoxythymidine (AZT).

5. The method of claim 1, wherein the NRTI inhibits mitochondrial polymerase γ.

6. The method of claim 1, wherein the NRTI increases the rate of mitochondrial DNA mutations.

7. The method of claim 1, wherein administration of the composition comprising a water soluble extract from a fruit of genus *Elaeis* or one or more phenolic compounds present in a water soluble extract from a fruit of genus *Elaeis* decreases the rate of mitochondrial DNA mutations.

8. The method of claim 1, wherein one or more phenolic compounds present in a water soluble extract from a fruit of genus *Elaeis* is administered, and said one or more phenolic compounds are natural or synthetic.

9. The method of claim 1, further comprising determining whether the subject has a mitochondrial DNA mutation.

* * * * *

SEQUENCE LISTING

<160> NUMBER OF SEQ ID NOS: 41

<210> SEQ ID NO 1
<211> LENGTH: 28
<212> TYPE: DNA
<213> ORGANISM: Artificial sequence
<220> FEATURE:
<223> OTHER INFORMATION: primer

<400> SEQUENCE: 1
aaagcggtgt gtgtgtgctg ggtaggat                                      28

<210> SEQ ID NO 2
<211> LENGTH: 27
<212> TYPE: DNA
<213> ORGANISM: Artificial sequence
<220> FEATURE:
<223> OTHER INFORMATION: primer

<400> SEQUENCE: 2
acttcagggt cataaagcct aaatagc                                       27

<210> SEQ ID NO 3
<211> LENGTH: 31
<212> TYPE: DNA
<213> ORGANISM: Artificial sequence
<220> FEATURE:
<223> OTHER INFORMATION: primer

<400> SEQUENCE: 3
aatagagggg gtagaggggg tgctataggg t                             31

<210> SEQ ID NO 4
<211> LENGTH: 28
<212> TYPE: DNA
<213> ORGANISM: Artificial sequence
<220> FEATURE:
<223> OTHER INFORMATION: primer

<400> SEQUENCE: 4
tccttatctg cttcctagtc ctgtatgc                                 28

<210> SEQ ID NO 5
<211> LENGTH: 37
<212> TYPE: DNA
<213> ORGANISM: Artificial sequence
<220> FEATURE:
<223> OTHER INFORMATION: primer

<400> SEQUENCE: 5
aacataagaa cagggaggtt agaagtaggg tcttggt                       37

<210> SEQ ID NO 6
<211> LENGTH: 18
<212> TYPE: DNA
<213> ORGANISM: Artificial sequence
<220> FEATURE:
<223> OTHER INFORMATION: primer

<400> SEQUENCE: 6
cgccccgacc ttagctct                                            18

<210> SEQ ID NO 7
<211> LENGTH: 590
<212> TYPE: DNA
<213> ORGANISM: Homo sapiens

<400> SEQUENCE: 7
gctcgccaca cacacacgac ccatcctacc cgcccccaac ataactactc taatcatcat    60
accctcaccc tcccctttta ttacacaatc aaccccccac tgacaatttt cacgtatggc   120
ggttttctat tttaaacttt agaccaatcc gaccacaatc caagaaaca aaaaccccaa    180
accgtctcta cacaaattca cgacaccggt cttcgccccc tccccccaa accaccttta    240
aaaaacaata ctacagacac acctttcacc gacacgtctg taagttaaca ataataatac   300
aggatgttcg taattaatta attgtgtgaa atcattcata caagcggaca ttataacttg    360
catccacgct atttattatc ctactccgtc cttagtttct gtctatgacg ctgtatccca    420
cgaggccgag gtcgcagagc gttacgatag cgcacgtatg gggggtctgc ttttatggtt    480
tacgtacctc tcgagggcac tcaccaatta tcccactatc tggacactag gtagcactac    540
agaataaatt cccccttgcac acccgataaa tcgaaatac tgggacttca               590

<210> SEQ ID NO 8
<211> LENGTH: 616
<212> TYPE: DNA
<213> ORGANISM: Homo sapiens

<400> SEQUENCE: 8
cccgagatct cccccatctc ccccacgata tcccatttat gcccgggata agtttctaa     60

-continued

```
aaatccccctt aattaagatc ctgctacccg tactttgaca ccaaacgagg tgtctaaagt    120
ctcgtaactg gcatcatatg ggggccagca catcgccact ttcaccaaac caaatctgca    180
ggcccttaac gtagacaaaa attcggatta caccccctgtc gagtactcac gttctgcaga    240
acactacatt aataatatgc ttaccccccga agttagccct catgatgagc taacagttgc    300
agttcctcag cgtccagcgg accaagatcc ttattacccc cttcatacat cctcaacttc    360
taatcaggcg gcatcagcca catgagcatc caagtcatgg taaccaccgg ttaactaaac    420
taccattccc tccctagcaa ctggagcaga caatacattt cctacgcatc cctaccctcc    480
cgctactcct gatcctacta ccgcccgtcc tatcaagtct gccaaagata aaggactcgc    540
agactctaca atcataatca atcaaaacaa cactcacaat cctttttcccg tatgtcctga    600 tccttcgtct attcct    616
```

<210> SEQ ID NO 9
<211> LENGTH: 599
<212> TYPE: DNA
<213> ORGANISM: Homo sapiens

<400> SEQUENCE: 9

```
aagtattctt gtccctccaa tcttcatccc agaaccactg ttttatacaa cacatctcaa     60 gtccccctctc acgcagtata caacaaggat ccttctaaca tcaccactcc cacaaataat    120
attattacaa acacataagc cgatacttct tatcccgctt ccccggacgc cgcataagct    180
acaacttcgg actctgatca agcctgaggg gaagccgttc cagcttcccc caagccaacc    240
agagacgatc acacctctat ttagtataat accggttccc agtactaccg tcctcattag    300
tctccacaag aacacaacac tattcccacc tctccaattt cctcggtgaa taatcattac    360
aactatcatc ttactaccga tcccactgaa gtatactcta acaaacccga tgacgagcgt    420
cacgcggcta gtcccgcatc aaactcaaac tacgagtggg actagtctcc taactcattt    480
gccgatccga tctccaccga tcttatttat cctccggatc caactccaac tggtcccccca    540 acccataccc ctcccccccaa gtatcatctt ctcgctacca ctctcgattc cagcccccgc    599
```

<210> SEQ ID NO 10
<211> LENGTH: 28
<212> TYPE: DNA
<213> ORGANISM: Artificial sequence
<220> FEATURE:
<223> OTHER INFORMATION: probe

<400> SEQUENCE: 10

```
tggttagggt tctttatttt ggggttca    28
```

<210> SEQ ID NO 11
<211> LENGTH: 24
<212> TYPE: DNA
<213> ORGANISM: Artificial sequence
<220> FEATURE:
<223> OTHER INFORMATION: probe

<400> SEQUENCE: 11

```
aatgtgaaat ctgcttgggc tggt    24
```

<210> SEQ ID NO 12
<211> LENGTH: 29
<212> TYPE: DNA
<213> ORGANISM: Artificial sequence
<220> FEATURE:
<223> OTHER INFORMATION: probe

```
<400> SEQUENCE: 12
aatggcagag atgtctttaa gtgctgttt                                    29

<210> SEQ ID NO 13
<211> LENGTH: 25
<212> TYPE: DNA
<213> ORGANISM: Artificial sequence
<220> FEATURE:
<223> OTHER INFORMATION: probe

<400> SEQUENCE: 13
ggctaggagt tggggagggc gggtt                                        25

<210> SEQ ID NO 14
<211> LENGTH: 29
<212> TYPE: DNA
<213> ORGANISM: Artificial sequence
<220> FEATURE:
<223> OTHER INFORMATION: probe

<400> SEQUENCE: 14
aaatgtaatc gcgttcatat cacccagtt                                    29

<210> SEQ ID NO 15
<211> LENGTH: 25
<212> TYPE: DNA
<213> ORGANISM: Artificial sequence
<220> FEATURE:
<223> OTHER INFORMATION: probe

<400> SEQUENCE: 15
acgagagtac ccaacgcatg gagag                                        25

<210> SEQ ID NO 16
<211> LENGTH: 29
<212> TYPE: DNA
<213> ORGANISM: Artificial sequence
<220> FEATURE:
<223> OTHER INFORMATION: probe

<400> SEQUENCE: 16
taattgaaca taggtacgat aaataatta                                    29

<210> SEQ ID NO 17
<211> LENGTH: 25
<212> TYPE: DNA
<213> ORGANISM: Artificial sequence
<220> FEATURE:
<223> OTHER INFORMATION: probe

<400> SEQUENCE: 17
tttagtaaat gtgttcacct gtaat                                        25

<210> SEQ ID NO 18
<211> LENGTH: 29
<212> TYPE: DNA
<213> ORGANISM: Artificial sequence
<220> FEATURE:
<223> OTHER INFORMATION: probe

<400> SEQUENCE: 18
aactgggtga aaagtgacta tgcggactt                                    29

<210> SEQ ID NO 19
```

```
<211> LENGTH: 25
<212> TYPE: DNA
<213> ORGANISM: Artificial sequence
<220> FEATURE:
<223> OTHER INFORMATION: probe

<400> SEQUENCE: 19
tgggggaagt tttttcttat tatgt                                           25

<210> SEQ ID NO 20
<211> LENGTH: 29
<212> TYPE: DNA
<213> ORGANISM: Artificial sequence
<220> FEATURE:
<223> OTHER INFORMATION: probe

<400> SEQUENCE: 20
aaactactcg attatcaacg tcaaggatt                                       29

<210> SEQ ID NO 21
<211> LENGTH: 25
<212> TYPE: DNA
<213> ORGANISM: Artificial sequence
<220> FEATURE:
<223> OTHER INFORMATION: probe

<400> SEQUENCE: 21
gtcgcaggac gcctagtttt aggaa                                           25

<210> SEQ ID NO 22
<211> LENGTH: 29
<212> TYPE: DNA
<213> ORGANISM: Artificial sequence
<220> FEATURE:
<223> OTHER INFORMATION: probe

<400> SEQUENCE: 22
aaaatggggg aagtttgtat gagttgatt                                       29

<210> SEQ ID NO 23
<211> LENGTH: 24
<212> TYPE: DNA
<213> ORGANISM: Artificial sequence
<220> FEATURE:
<223> OTHER INFORMATION: probe

<400> SEQUENCE: 23
agataagttc gctgtattcg gtgt                                            24

<210> SEQ ID NO 24
<211> LENGTH: 29
<212> TYPE: DNA
<213> ORGANISM: Artificial sequence
<220> FEATURE:
<223> OTHER INFORMATION: probe

<400> SEQUENCE: 24
aaacgattgg ggactttaat tgggagttt                                       29

<210> SEQ ID NO 25
<211> LENGTH: 22
<212> TYPE: DNA
<213> ORGANISM: Artificial sequence
<220> FEATURE:
<223> OTHER INFORMATION: probe

<400> SEQUENCE: 25
```
agacgtctta tgttgtaatt at                                              22

<210> SEQ ID NO 26
<211> LENGTH: 29
<212> TYPE: DNA
<213> ORGANISM: Artificial sequence
<220> FEATURE:
<223> OTHER INFORMATION: probe

<400> SEQUENCE: 26
tttgtaaaga atgcgtagag ataggagaa                                       29

<210> SEQ ID NO 27
<211> LENGTH: 25
<212> TYPE: DNA
<213> ORGANISM: Artificial sequence
<220> FEATURE:
<223> OTHER INFORMATION: probe

<400> SEQUENCE: 27
gaggcattgt tcacgtcgtt tgtta                                           25

<210> SEQ ID NO 28
<211> LENGTH: 29
<212> TYPE: DNA
<213> ORGANISM: Artificial sequence
<220> FEATURE:
<223> OTHER INFORMATION: probe

<400> SEQUENCE: 28
tttttatacg tacggcaatt acatctgaa                                       29

<210> SEQ ID NO 29
<211> LENGTH: 25
<212> TYPE: DNA
<213> ORGANISM: Artificial sequence
<220> FEATURE:
<223> OTHER INFORMATION: probe

<400> SEQUENCE: 29
tttttaaatt taatatgggg atagc                                           25

<210> SEQ ID NO 30
<211> LENGTH: 24
<212> TYPE: DNA
<213> ORGANISM: Artificial sequence
<220> FEATURE:
<223> OTHER INFORMATION: probe

<400> SEQUENCE: 30
agtgaccata atatacctcc ggct                                            24

<210> SEQ ID NO 31
<211> LENGTH: 25
<212> TYPE: DNA
<213> ORGANISM: Artificial sequence
<220> FEATURE:
<223> OTHER INFORMATION: probe

<400> SEQUENCE: 31
tcgtatagtg gtcaatgtgg tatgg                                           25

<210> SEQ ID NO 32
<211> LENGTH: 29
<212> TYPE: DNA

```
<213> ORGANISM: Artificial sequence
<220> FEATURE:
<223> OTHER INFORMATION: probe

<400> SEQUENCE: 32
aagttcggtt ggttttttgct ggtgtggtt                                           29

<210> SEQ ID NO 33
<211> LENGTH: 19
<212> TYPE: DNA
<213> ORGANISM: Artificial sequence
<220> FEATURE:
<223> OTHER INFORMATION: probe

<400> SEQUENCE: 33
ttcggcaatg tcgaggggg                                                       19

<210> SEQ ID NO 34
<211> LENGTH: 29
<212> TYPE: DNA
<213> ORGANISM: Artificial sequence
<220> FEATURE:
<223> OTHER INFORMATION: probe

<400> SEQUENCE: 34
aatatgaaga atagagcgaa gaggccttt                                            29

<210> SEQ ID NO 35
<211> LENGTH: 25
<212> TYPE: DNA
<213> ORGANISM: Artificial sequence
<220> FEATURE:
<223> OTHER INFORMATION: probe

<400> SEQUENCE: 35
gcggcctatt ccatgttgac gcctg                                                25

<210> SEQ ID NO 36
<211> LENGTH: 29
<212> TYPE: DNA
<213> ORGANISM: Artificial sequence
<220> FEATURE:
<223> OTHER INFORMATION: probe

<400> SEQUENCE: 36
ttaaggttgt agtgatgggg gtgtttaaa                                            29

<210> SEQ ID NO 37
<211> LENGTH: 25
<212> TYPE: DNA
<213> ORGANISM: Artificial sequence
<220> FEATURE:
<223> OTHER INFORMATION: probe

<400> SEQUENCE: 37
ttataataat ctttgtgttt tcggc                                                25

<210> SEQ ID NO 38
<211> LENGTH: 29
<212> TYPE: DNA
<213> ORGANISM: Artificial sequence
<220> FEATURE:
<223> OTHER INFORMATION: probe

<400> SEQUENCE: 38
aattgatcaa ggggtttggt atagggatt                                            29
```

```
<210> SEQ ID NO 39
<211> LENGTH: 25
<212> TYPE: DNA
<213> ORGANISM: Artificial sequence
<220> FEATURE:
<223> OTHER INFORMATION: probe

<400> SEQUENCE: 39
gggaggttta tgtaaaaga gagat                                          25

<210> SEQ ID NO 40
<211> LENGTH: 29
<212> TYPE: DNA
<213> ORGANISM: Artificial sequence
<220> FEATURE:
<223> OTHER INFORMATION: probe

<400> SEQUENCE: 40
ttagataaac catagtatgt ccgagggaa                                     29

<210> SEQ ID NO 41
<211> LENGTH: 25
<212> TYPE: DNA
<213> ORGANISM: Artificial sequence
<220> FEATURE:
<223> OTHER INFORMATION: probe

<400> SEQUENCE: 41
tcatgattgc agtagtggta agagg                                         25
```